United States Patent [19]

Passaro et al.

[11] Patent Number: 4,687,934
[45] Date of Patent: Aug. 18, 1987

[54] INFRARED GAS ANALYZER WITH AUTOMATIC ZERO ADJUSTMENT

[75] Inventors: Robert E. Passaro, Richmond; Raymond E. Rogers, Oakland; Craig J. Griffith, Berkeley, all of Calif.

[73] Assignee: Andros Analyzers Incorporated, Berkeley, Calif.

[21] Appl. No.: 818,342

[22] Filed: Jan. 10, 1986

[51] Int. Cl.$^4$ .......................... G01J 1/00; G01D 18/00
[52] U.S. Cl. .................................. 250/343; 250/252.1
[58] Field of Search ............... 250/252.1, 338 R, 339, 250/341, 343, 344, 345

[56] References Cited

U.S. PATENT DOCUMENTS

| | | | |
|---|---|---|---|
| 2,829,268 | 4/1958 | Chope | 250/252.1 |
| 3,812,330 | 5/1974 | Bowman et al. | 250/252.1 |
| 4,013,260 | 3/1977 | McClatchie et al. | 250/343 |
| 4,233,513 | 11/1980 | Elder et al. | 250/343 |
| 4,346,296 | 8/1982 | Passaro et al. | 250/343 |
| 4,398,091 | 8/1983 | Passaro et al. | 250/343 |

*Primary Examiner*—Janice A. Howell
*Attorney, Agent, or Firm*—Fitch, Even, Tabin & Flannery

[57] ABSTRACT

Automatic zeroing apparatus zeroes an infrared gas analyzer automatically upon the occurrence of preselected conditions to indicate zero in the absence of absorption of infrared radiation by a gas mixture being analyzed. The gas analyzer has a sample cell for containing a gas mixture to be analyzed. Infrared radiation directed through the sample cell is detected at a preselected wavelength to produce a detection signal. A signal processor outputs a signal systematically related to the difference between the detection signal and a reference signal. For zeroing the sample cell is filled with gas substantially nonabsorbent of infrared radiation at the respective characteristic wavelength. A comparator produces an error signal when the output signal differs from zero. A gain control automatically controls the signal level of the detection signal to reduce the output signal substantially to zero with the nonabsorbent gas filling the sample cell. The preselected conditions may include the passage of a predetermined time and a temperature drift beyond a predetermined limit.

22 Claims, 21 Drawing Figures

| | READY | PUMP & SOLENOID | ZERO REQUEST |
|---|---|---|---|
| 402 WARM UP | 0 | 1 | 0 |
| 406 ZERO | 0 | 1 | 0 |
| 404 SYSTEM FAULT | 0 | 0 | 0 |
| 408 NORMAL | 1 | 0 | 0 |
| 410 ZERO REQUEST | BLINK | 0 | 1 |
| 412 PURGE | 0 | 1 | 0 |
| 414 WAIT | BLINK | 0 | 0 |

# INFRARED GAS ANALYZER WITH AUTOMATIC ZERO ADJUSTMENT

BACKGROUND OF THE INVENTION

This invention relates to infrared gas analyzers and more particularly to such gas analyzers with an automatic zero adjustment. Still more particularly it relates to such gas analyzers having multiple channels using a programmable microprocessor for performing the zero adjustment.

Infrared gas analyzers typically utilize an infrared source to direct infrared energy through a mixture of unknown gases contained in a sample cell. The infrared energy passing through the mixture in the sample cell at one or respective frequencies is measured as indicative of the relative concentrations of respective gases in the mixture, the respective gases exhibiting different absorption characteristics at respective frequencies. That is, the absorption by respective gases is frequency dependent.

One such analyzer is described in Passaro, et al., U.S. Pat. No. 4,346,296. As there described, an infrared source emits infrared at relatively constant intensity over a relatively broad spectrum. The infrared radiation from the source is interrupted periodically by a chopper. After passing through the sample cell, the chopped infrared is detected by respective detectors. In each case the radiation is filtered by a narrow band-pass filter so that such detector is effectively sensitive only to radiation of a particular narrow band of frequencies corresponding to a respective absorption frequency characteristic of a respective gas. The respective detection signals are thus systematically related to the relative concentration of the respective gases. Because of the chopper, these signals are AC signals at the chopper frequency. The signals are amplified, detected (rectified) and filtered to produce corresponding DC signals. Each filtered signal is applied to one input of a so-called span amplifier, which comprises a summing amplifier with an offset reference input and a controllable feedback input. The offset offsets the zero point, and the feedback controls span or the magnitude of input signal required for full scale output. The signal input has a gain control to control the point at which the signal input balances out the offset signal and hence the zero point of the span amplifier. That is the point where there is zero output from the span amplifier in the absence of absorption of the incident infrared radiation. The output of the span amplifier is proportional to the difference between the detection signal (after the gain control) and the offset signal. It may be noted that difference includes the addition of signals of opposite polarities. The amplifier output is measured by a meter, which may be a recorder, which is calibrated to indicate the relative concentration of the respective gas.

As described in the aforesaid U.S. Pat. No. 4,346,296, the zero point of the span amplifier is adjusted, that is, the instrument is zeroed, by introducing a so-called zero gas into the sample cell and adjusting the gain control of the signal input to provide a zero meter reading. The zero gas is a gas, such as nitrogen, which is substantially nonabsorptive of infrared radiation, at least at the frequencies passed by the respective filters. When a predetermined calibrating gas is introduced into the sample cell, the gain of the feedback signal is adjusted to some predetermined calibrated value. Then when the gas to be analyzed is introduced, the output meter properly records or indicates the relative concentrations of the respective constituent gas. For the purposes of checking the span calibration a push-button switch was operated to put a fixed input into the summing span amplifier and the resultant meter reading set at a predetermined level by adjusting the span control in the feedback loop.

SUMMARY OF THE INVENTION

A problem with the gas analyzer of the aforesaid patent was that the zero point drifted from time to time, requiring intervention by an operator to return the system to a proper zero condition. Drift is caused by changes in the infrared source, the sample cell, other parts of the radiation path and the detection system. Such changes may be occasioned by temperature drift. This prior system required that the operator note the occurrence of changes or follow a schedule and perform manual zeroing on a regular basis or as needed. In any event, human presence and attention was required.

In accordance with the present invention zeroing of the system is performed automatically. Under the control of a programmable microprocessor each of any number of channels, three, for example, are zeroed periodically and/or upon temperature drift. More particularly, the system operates as a satellite to a host. The microprocessor provides for warm-up delays and then enters a zeroing mode repeated after each predetermined period or upon temperature drift above a predetermined level or upon intervention by the host.

In the zeroing mode the microprocessor provides signals calling for zero gas to fill the sample cell and then controls the gain of the signal input to a summing amplifier to provide a zero output from the span amplifier as determined by a comparator. Such gain control is effected by controlling the multiplying factor of a multiplying digital to analog converter (MDAC or DAC). The factor is determined independently for each channel and is stored in the microprocessor.

Upon completion of zeroing, the system enters its normal measuring regime. The gas to be analyzed is passed into the sample cell. Separate detection systems are provided for each channel, with appropriate multiplexing so that a single DAC can be used for all channels. For each channel the respective factor is provided by the DAC at the appropriate times during measuring. The output signals from the respective amplifiers are then provided to the host, and there applied to respective calibrated meters and/or recorders which thereupon indicate respective relative concentration of the constituents of the gas being analyzed.

Provision is made for span adjustment and electronic calibration. Provision is also made for disabling the zeroing operation under certain conditions, as upon electronic calibration or during emissions testing.

Thus, an important aspect of the present invention is the automatic zeroing of an infrared gas analyzer.

Still another aspect is the automatic zeroing of an infrared gas analyzer with hysteresis.

Another aspect is providing such automatic zeroing under the control of a programmable microprocessor.

Another aspect is the control of a single multiplying digital to analog converter for the automatic zeroing of multiple channels of an infrared gas analyzer.

Another aspect is the automatic zeroing of such gas analyzer system periodically and/or upon a predetermined ambient temperature charge.

Other aspects, objects and advantages of the the present invention will become clear from the following detailed description, particularly when taken in connection with the accompanying drawings.

DETAILED DESCRIPTION

Figure 1:
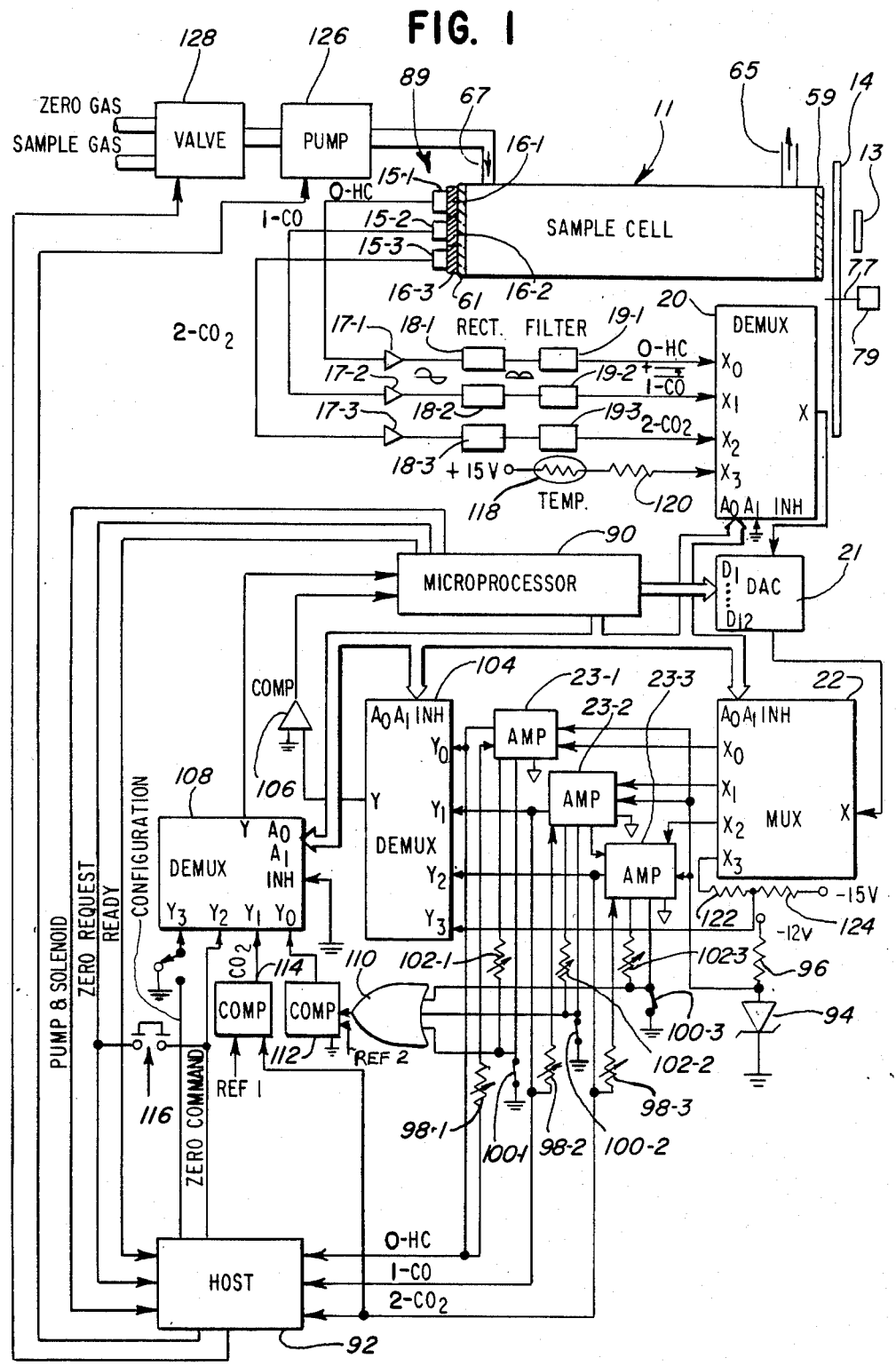
FIG. 1 is a simplified illustration, partly diagrammatic, of an infrared gas analyzer system including automatic zeroing in accordance with the present invention.

Generally, as shown in FIG. 1, the infrared gas analyzer system of the present invention includes a sample cell 11 for containing a gas mixture to be analyzed. A source 13 directs infrared radiation through the sample cell 11, and the infrared radiation is periodically interrupted by a chopper 14 at a predetermined frequency. A detection signal is produced by each of detectors 15-1, 15-2, and 15-3 corresponding to the infrared radiation received at a respective preselected wavelength, such signal being an AC signal having an amplitude monotonically related to the infrared radiation passing through the sample cell at that wavelength and having a frequency corresponding to the predetermined frequency of the chopper 14. The preselected wavelength corresponds to the characteristic absorption wavelength of the respective gas it is desired to detect in the sample mixture. Such selection is effected by respective narrow band pass filters. The AC signal outputs of the detectors are processed to produce respective DC signals having amplitudes systematically related to the concentration of the respective gas to be detected. Each AC signal is amplified by a respective amplifier 17-1, 17-2, 17-3, full-wave rectified by a respective full-wave rectifier 18-1, 18-2, 18-3 and filtered by a respective filter 19-1, 19-2, 19-3 to produce the corresponding DC signals. The DC signals are applied through a demultiplexer 20 to a gain control in the form of a multiplying DAC 21. The DAC 21 adjusts the gains of the respective channels, and the adjusted signals are applied through a multiplexer 22 to respective span amplifiers 23-1, 23-2, 23-3. The outputs of the span amplifiers are transmitted to a host 92 where they are applied to respective meters and/or recorders calibrated to read relative concentrations of the respective gases.

Figure 2:
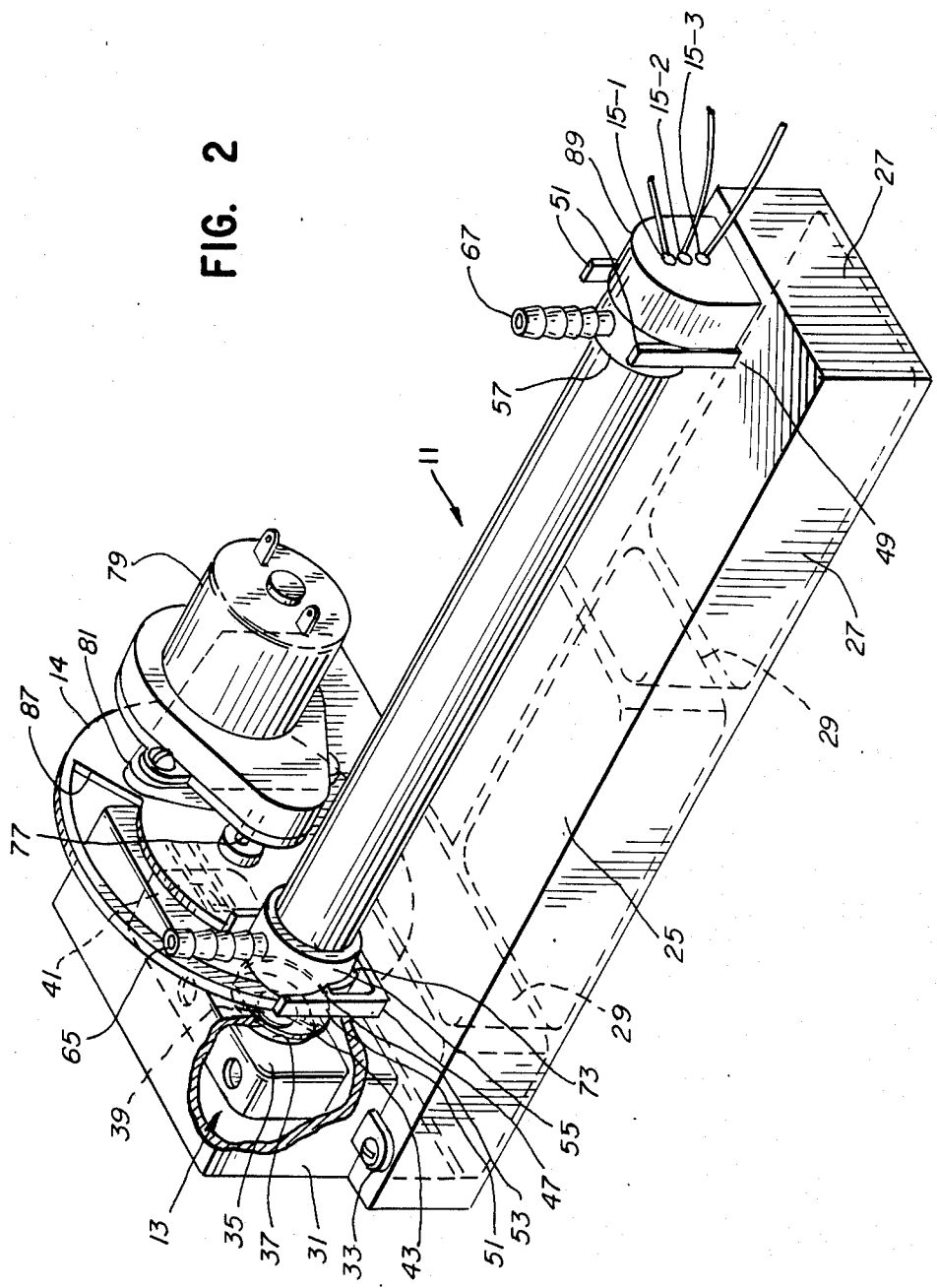
FIG. 2 is an isometric drawing of the source, sample cell and detector arrangement of the gas analyzer system shown in FIG. 1, with a portion broken away.

In FIG. 2 is illustrated a sample cell 11 showing the physical disposition of the source 13, chopper 14, and detectors 15-1, 15-2 and 15-3 and filters relative thereto. This part of the system may be substantially the same as the corresponding part of the system shown in the aforesaid patent, except that there are three channels rather than two.

The preferred embodiment of the present invention is for detecting the relative presence of three gases in the exhaust gas of an automobile engine. The three gases may be hydrocarbons, carbon monoxide and carbon dioxide, but the invention is not limited to use in connection with such specific gases, nor is it limited to use in connection with the exhaust gas of an automobile engine. There will be other uses, apparent to those skilled in the art, for the analyzer of the invention where a low cost unit of the type described will be acceptable.

The sample cell unit is mounted on a base plate 25 having a generally rectangular shape and having rigidizing walls 27 at its periphery connected by rigidizing cross webs 29. At one end of the unit, the infrared source 13 is shown mounted in a source housing 31 secured to the base plate by mounting brackets 33. The source 13 includes a plate 35 having a reflecting recess 37 of parabolic, conical or other suitable shape to reflect the infrared energy into a beam. The source element 39, which may be of any suitable type, is mounted on a holder 41. Suitable electrical connection is made to energize the source element by means not shown. The source housing 31 includes a window 43 for transmitting infrared radiation from the source element out of the housing. The window may be of any material substantially transparent to infrared radiation at the wavelengths of interest.

The sample cell 11 is mounted on a pair of roughly U-shaped mounting clips 47, 49 attached to the base plate and is in alignment with the infrared energy eminating from the infrared source 13. Each of the clips 47, 49 comprises a pair of upright tines 51 which are resilient and which have projections 53 extending inwardly therefrom. The resilient tines enable the sample cell 11 to be easily removed from the device for replacement or cleaning. Each end of the sample cell 11 is provided with an end sleeve 55, 57, respectively, each of which retains in place a window 59, 61, respectively, transparent to infrared radiation. A suitable material for the windows is, for example, mica. A coupling 65, 67, respectively, is mounted in each end sleeve 55, 57, for permitting exhaust gas from the automobile engine exhaust being analyzed to pass into and out of the sample cell 11.

Each of the sleeves 55, 57 is provided with a semi-annular collar 73 which wraps approximately 180° around the underside of each sleeve and extends axially about one half the length of the sleeve. The collars 73, with the sample cell 11 in the operative position, engage the underside of the projections 53, to retain the sample cell in place. However, since the sample cell 11 will, during use, become dirty from the exhaust gas being analyzed, it is desirable that it be easily cleaned or even replaced. By merely separating the tines 51 so the projections 53 clear the collars 73, the sample cell 11 may be easily removed or installed.

The end of the sample cell assembly adjacent the source housing 31 is spaced a short distance therefrom so as to enable the interposition of the chopper wheel 14. The chopper wheel 14 is rotatably mounted on the spindle 77 of a drive motor 79 which, in turn, is mounted to the base plate 25 by a motor mount bracket 81. The chopper wheel 14 comprises a circular opaque disk which may be any suitable construction to interrupt periodically the infrared energy emanating from the source. However, it is preferred that the disk have a cut-out region 87 of generally arcuate shape extending through 180° of the wheel rotation. In this way, the beam is blocked 50% of the time during each rotation. The chopper thus provides an AC signal, which has the effect of cancelling out any background DC radiation. Of course, other types of chopper wheels may be used, such as ones having two 90° cut-out regions, to provide the same duty cycle.

The end of the sample cell 11 opposite the source 13 is abutted flush against a filter and detector block 89. The block 89 is secured by suitable means to the base plate. The block 89 is generally cylindrical in shape and is axially aligned with the sample cell 11. The block 89 contains the filters 16-1, 16-2, 16-3 disposed side by side in alignment with radiation passing through the sample cell 11. The filters pass infrared energy of the characteristic absorption wavelengths of the gases of interest, for example, hydrocarbons, carbon monoxide and carbon dioxide.

Immediately behind the filters are mounted the detectors 15-1, 15-2, 15-3, which may be of any suitable construction. The detectors provide an output which is systematically related (e.g., proportional) to the magnitude of the infrared energy passing through the corresponding filter. Thus, the output of each of the detectors comprises an AC signal, the amplitude of which is systematically related to the energy at the respective frequency passing through the sample cell 11.

Referring now more particularly to FIG. 1, a form of the signal processor used in the apparatus of the invention is shown. The output of each detector 15-1, 15-2, 15-3, which is a substantially square wave signal having the frequency of the rotation of the chopper wheel 14, varies between nearly zero and a negative (or in certain embodiments positive) voltage. This signal is applied to the respective preamplifier 17-1, 17-2, 17-3 by which it is suitable amplified.

Figure 3:
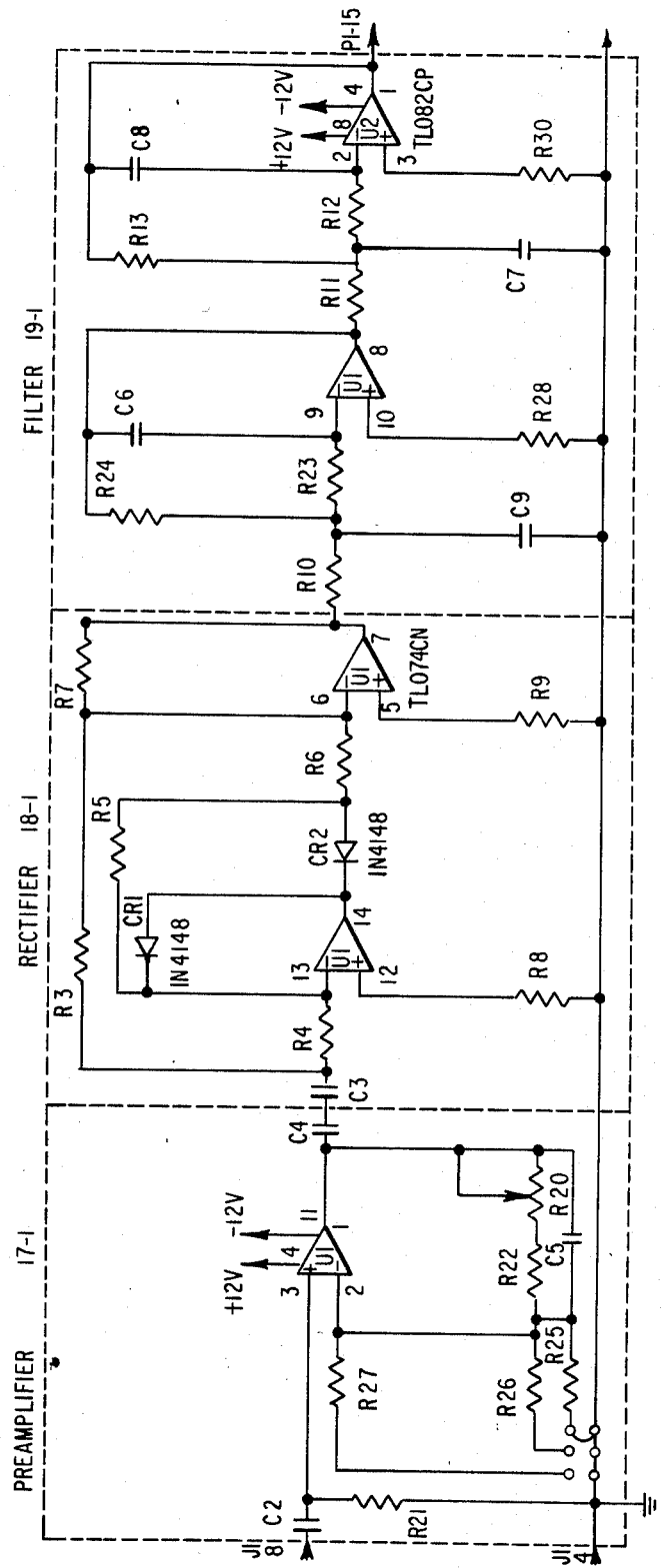
FIG. 3 is a detailed electrical schematic diagram of preferred forms of preamplifier, rectifier and filter shown in FIG. 1.

In the illustrated embodiment, each preamplifier may be in the form illustrated in FIG. 3. FIG. 3 illustrates the preamplifier 17-1; however, the preamplifiers 17-2 and 17-3 may be identical thereto. The AC signal from the respective detector 15-1 is applied at a terminal J1-8 through a coupling capacitor C2, and the amplified output is output through coupling capacitors C4 and C3.

The amplified signals are applied to respective full-wave rectifiers (demodulators) 18-1, 18-2, 18-3 which act to demodulate the signals. In the illustrated embodiment, each rectifier may be in the form illustrated in FIG. 3. FIG. 3 illustrates the rectifier 18-1; however, the rectifiers 18-2 and 18-3 may be identical thereto. The amplified signal from the preamplifier 17-1 is applied through the coupling capacitors C4 and C3, and the rectified signal is output through a resistor R10.

The rectified signals are applied to respective filters 19-1, 19-2, 19-3 which act to filter the rectified signals to corresponding DC signals. In the illustrated embodiment, each filter may be in the form illustrated in FIG. 3. FIG. 3 illustrates the filter 19-1; however, the filters 19-2 and 19-3 may be identical thereto. The rectified signal from the rectifieer 18-1 is applied through the resistor R10 and the filtered DC signal is output on a terminal P1-15.

Figure 4A:
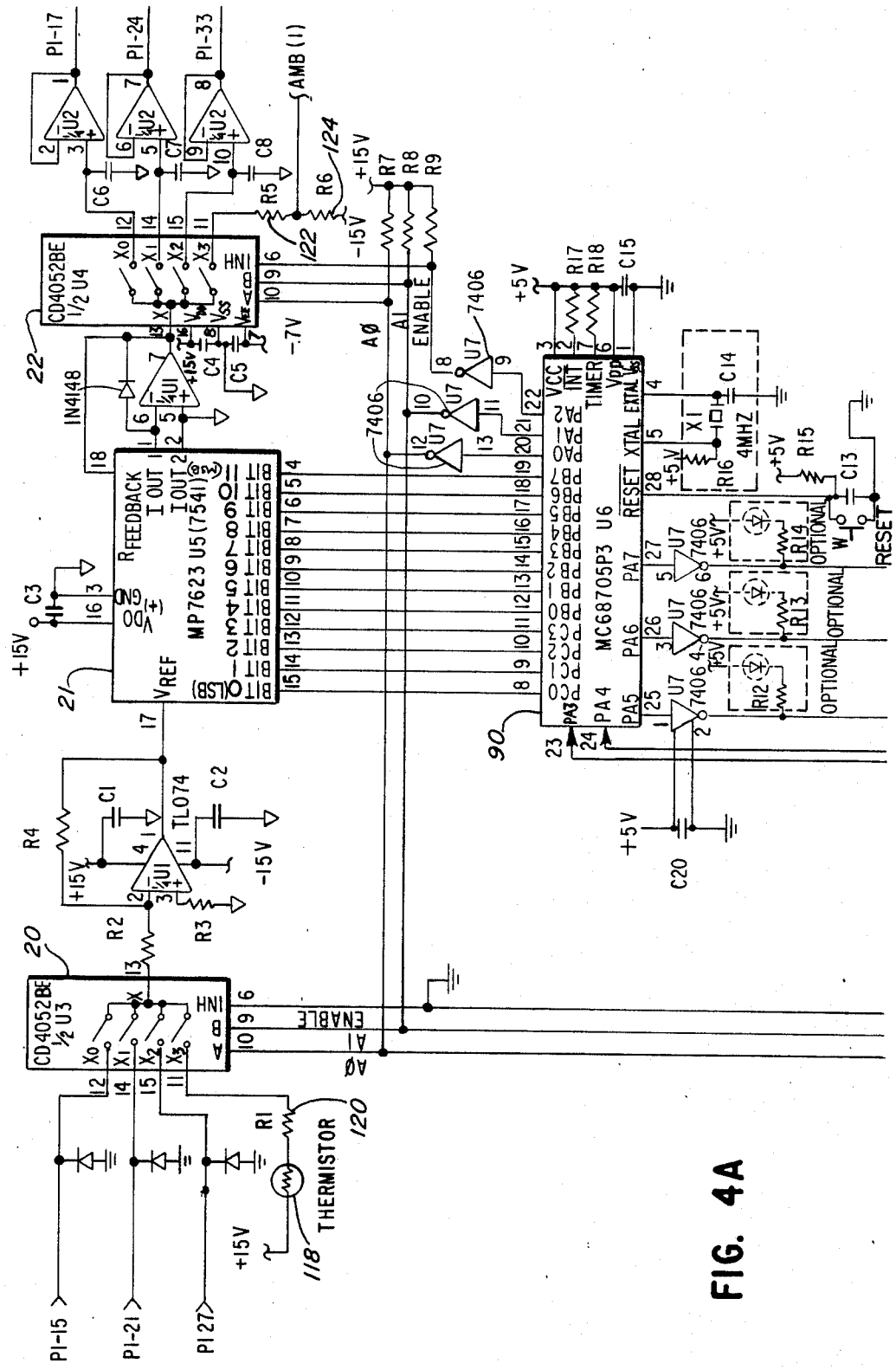
FIGS. 4A and 4B together are a detailed electrical schematic diagram of a preferred form of multiplexing, demultiplexing, DAC, comparator and microprocessor control shown in FIG. 1.
Figure 4B:
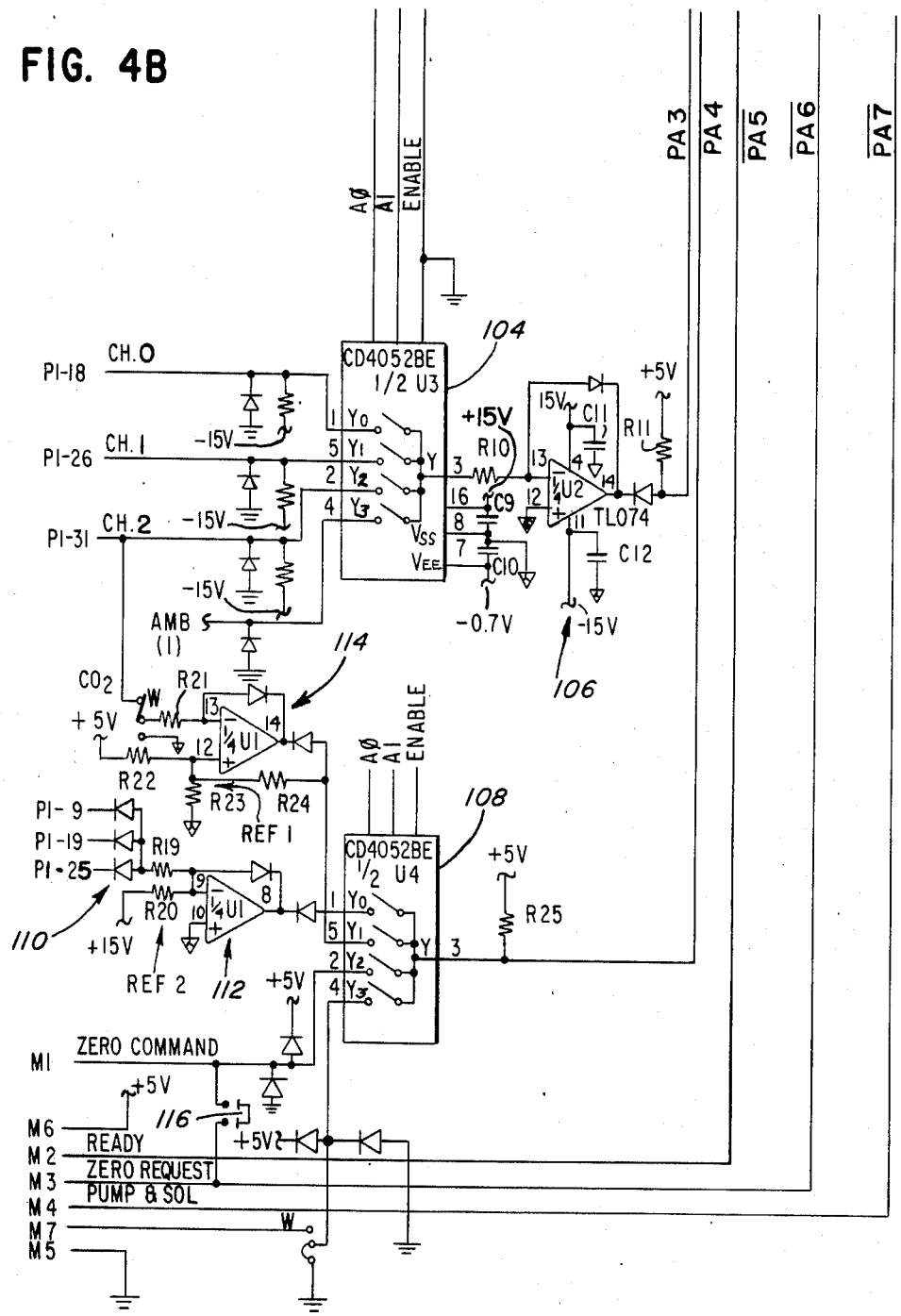

As shown with particularity in FIG. 4, the outputs from the filters 19-1, 19-2 and 19-3 are applied at respective terminals P1-15, P1-21 and P1-27 to the respective $X_0$, $X_1$ and $X_2$ input terminals of the demultiplexer 20, which may be, as shown, of the type CD4052BE, connected as shown. The input signals are demultiplexed under the control of control signals applied at terminals A and B of the demultiplexer 20 from a microprocessor 90. The multiplexer 20 connects a respective input terminal to the output terminal X as synchronized by the control signals. Thus, output signals at the terminal X are successive different input signals in a particular order. Each successive output signal is applied through an inverting amplifier U1-1,2,3 which acts to match impedances. The output of the amplifier is applied to the voltage reference terminal ($V_{REF}$) of the DAC 21, which may be of the type MP7623.

Figure 5:
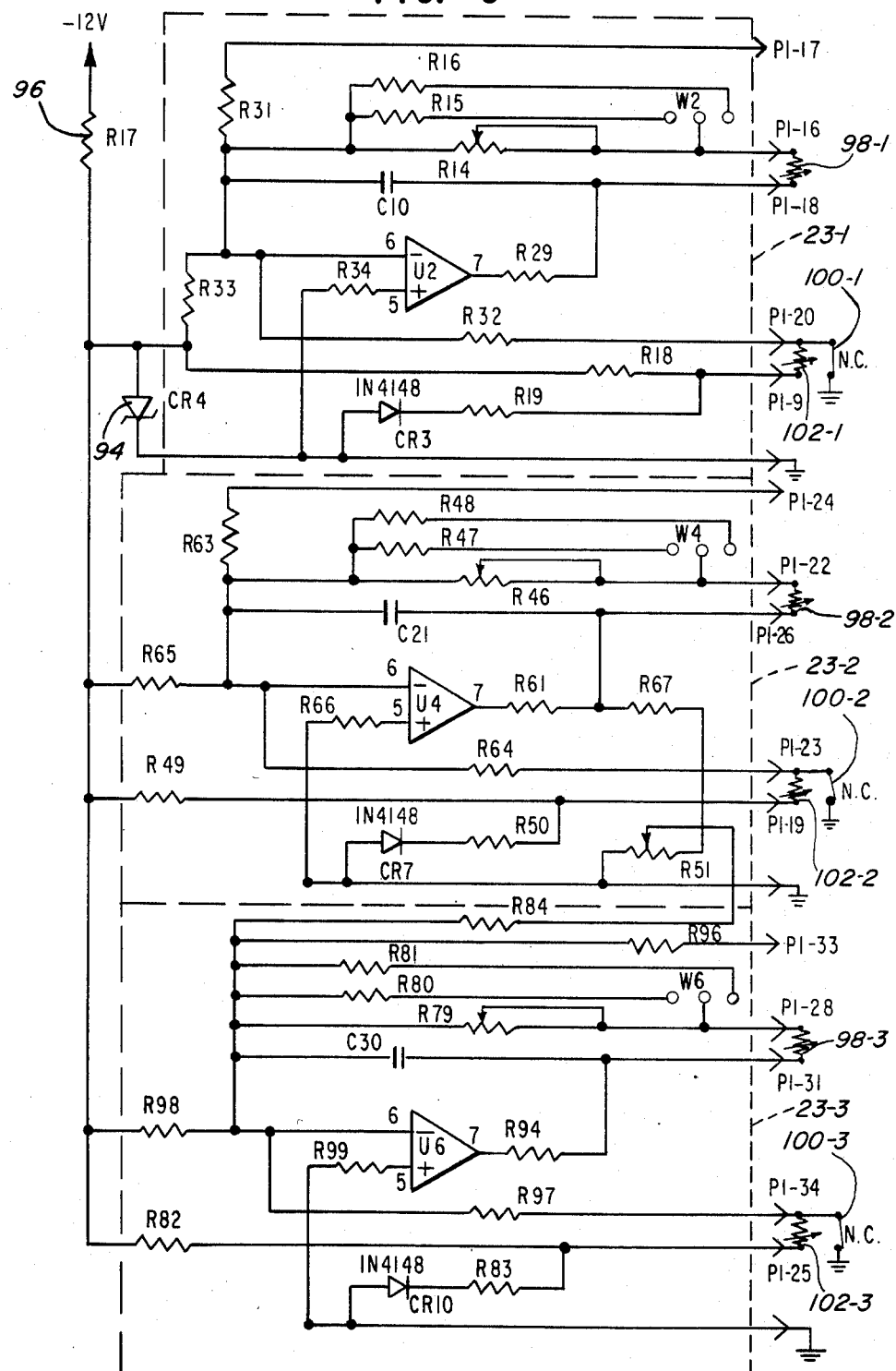
FIG. 5 is a detailed electrical schematic diagam of a preferred form of the span amplifiers shown in FIG. 1.

The DAC 21 operates to multiply the voltage on the voltage reference terminal by a factor determined by the digital inputs to input terminals BIT 0 to BIT 11 from the microprocessor 90. How these inputs are determined will be explained below. Suffice to state here that the product appears as current outputs at terminals I out 1 and I out 2. These outputs are applied to a differential current amplifier U1-5,6,7, the output of which is a voltage proportional to the product of the signal from the multiplexer 20 and the factor from the microprocessor 90. This output is fed back to the DAC 21 at its terminal $R_{FEEDBACK}$ and is also applied to the X terminal of the multiplexer 22, which is also preferably of type CD4052BE. The multiplexer 22 is also controlled by control signals applied to its terminals A and B from the microprocessor 90 in synchronism with the demultiplexer 20, with an additional signal applied to its inhibit terminal INH to inhibit the connection to the output terminal for brief periods during switching to prevent false signals. The multiplexer 22 provides signals for the respective channels at terminals $X_0$, $X_1$ and $X_2$. These are applied through respective sample and hold circuits U2-1,2,3, U2-5,6,7 and U2-8,9,10 to respective span amplifiers 23-1, 23-2 and 23-3 at terminals P1-17, P1-24 and P1-33, respectively. The outputs of the respective span amplifiers are transmitted over respective lines to the host 92 from terminals P1-18, P1-26 and P1-31, respectively (FIG. 5). In the example, the three channels are 0-hydrocarbons (HC), 1-carbon monoxide (CO)

and 2-carbon dioxide ($CO_2$). At the host the signals are applied to meters, which may include recorders, which are calibrated in a conventional manner to indicate the relative concentration of the respective gases in the sample being analyzed.

The preferred embodiments of the span amplifiers 23-1, 23-2 and 23-3 are illustrated in greater detail in FIG. 5. The signal inputs from the multiplexer 22 (after the sample and hold circuits) are applied at respective input terminals P1-17, P1-24 and P1-33 through respective input resistors R31, R63 and R96 to the summing junctions at the (−) inputs (U2-6, U4-6 and U6-6) of respective summing amplifiers U2-5,6,7, U4-5,6,7 and U6-5,6,7. A reference voltage is developed by a zener diode 94 from a voltage applied thereto from a −12 v source through a dropping resistor 96. This reference voltage is applied to the respective summing junctions through respective input resistors R33, R65 and R98. The span amplifier outputs appear at respective terminals P1-18, P1-26 and P1-31. In addition to being transmitted to the host 92, these signals are fed back to the respective summing juntions through respective external span adjust resistors 98-1, 98-2 and 98-3, which may be located in or at the host 92. The span adjust resistors are in series with respective variable resistors R14, R46 and R79 which are factory set for appropriate span adjustment range. The respective (+) terminals U2-5, U4-5 and U6-5 are connected to ground through respective resistors R34, R66 and R99.

Referring particularly to the span amplifier 23-1, the summing amplifier U2-5,6,7 operates to keep its summing junction U2-6 at ground potential. The current feedback through the resistors 98-1 and R14 balances the sum of the positive current from the signal input through the resistor R31 and the respective negative current to the voltage reference through the resistor R33. When channel 0 is properly zeroed, in a manner to be discussed below, the output signal at the terminal P1-18 is zero in the presence of zero gas, as indicated at the respective meter and/or recorder at the host 92. Then the presence of hydrocarbons in the sample cell 11 reduces the signal input at the terminal P1-17 accordingly, and the resulting unbalance gives rise to a proportionately related output signal at the terminal P1-18. The magnitude of this output is dependent upon the magnitude of the span adjust resistor 98-1. This span adjust resistor 98-1 is set by introducing a predetermined gas (hydrocarbons in this example) of known concentration into the sample cell 11 and adjusting the resistor 98-1 to the point where the meter reading at the host 92 is a value previously determined to indicate such predetermined concentration of the calibration gas. The meter and/or recorder is calibrated in a known manner so that all readings of the meter and/or recorder properly indicate the relative concentration of the particular gas. The other span amplifiers 23-2 and 23-3 operate in the same fashion; however, a small portion of the signal output from the amplifier 23-2 is picked off from a voltage divider consisting of resistors R67 and R51 and applied through an input resistor R84 to the summing junction U6-6 of the span amplifier 23-3 to compensate for the effect of carbon monoxide on the carbon dioxide measurement.

As an alternative to calibrating the system using a known gas of known concentration, the system can be calibrated electronically. Taking channel 0 as an example, with channel 0 properly zeroed and zero gas present in the sample cell 11, an additional known calibration signal current is applied to the summing junction U2-6 and the span adjust resistor 98-1 is adjusted accordingly. This additional calibration signal is applied through a resistor R32, which is normally grounded at a terminal P1-20 through a normally closed switch 100-1, so that no current is input through the resistor R32. When the switch is opened, the resistor R32 is connected through a variable resistor 102-1 and a resistor R18 to the voltage reference at the zener diode 94. This applies the calibration signal to the summing junction. The switch 100-1 and the variable resistor 102-1 may be in or at the host 92. The variable resistor 102-1 may be adjusted empirically to correspond to a predetermined hydrocarbous concentration in the sample cell 11. To this end, with the calibration gas filling the sample cell 11, the span adjust resistor 98-1 is adjusted for proper calibration. Then with zero gas in the sample cell 11 and the span adjust resistor in the position so determined, the switch 100-1 is opened and the variable resistor 102-1 set to give the same meter reading as during normal calibration with the calibration gas. Thereafter, whenever the span adjust resistor 98-1 gets out of the calibration position, it may be reset by electronic calibration by filling the sample cell 11 with zero gas and opening the switch 100-1 to apply the additional known calibration signal current and adjusting the span adjust resistor accordingly. It is unnecessary to have the calibration gas at hand. Channels 1 and 2 may be similarly calibrated using switches 100-2, 100-3 and variable resistors 102-2, 102-3.

As stated above, the measurements depend upon a proper zeroing of each channel. This requires the adjustment of each respective factor provided by the DAC 21 to produce zero output when the zero gas is in the sample cell 11. Such adjustment is effected by the microprocessor 90 in response to the outputs of the respective span amplifiers 23-1, 23-2, 23-3 at respective output terminals P1-18, P1-26 and P1-31 when zero gas is in the sample cell 11. The microprocessor is put in its zeroing routine, as will be described below. The outputs from terminals P1-18, P1-26 and P1-31 are applied through a demultiplexer 104 to a comparator 106. The comparator 106 compares the respective output signals with 0 or ground and outputs a binary 0 or 1 to indicate whether or not the signal is too large. The comparator output is input to the port PA3 of the microprocessor 90, which is programmed, as described below, to output on ports PC0-PB7 a binary signal that, when applied to the input ports BIT 0–BIT 11 of the DAC 21, produces zero output of the respective span amplifier 23-1, 23-2, 23-3. After each channel is thus zeroed, the system is returned to its normal measuring routine, as will be described below.

In the illustrated embodiment, the microprocessor 90 is of the type MC68705P3. Control signals therefor are applied to its port PA4 through a demultiplexer 108 which is timed by signals from the microprocessor in synchronism with the multiplexer 20. The timing signals for the multiplexer 22 and demultiplexers 20, 104 and 108 are derived from an internal clock within the microprocessor 90 (or an external clock, if desired), which may be at 4 MHz, and output from ports PA0-PA2.

There are four inputs to the demultiplexer 108. Terminal $Y_0$ receives a signal indicating that the system is performing an electronic calibration. As described above, when an electronic calibration is performed, one, or more usually all, of switches 100-1, 100-2, 100-3 are opened, lowering the voltages on respective terminals P1-9, P1-19 and P1-25, which are normally grounded when the switches are closed. The lowered voltage on one or more of these terminals is applied through a wired-OR gate 110 to a comparator 112 where it is combined with a reference voltage REF2 and compared to ground to develop an appropriate digital signal when the system is being electronically calibrated. Terminal $Y_1$ receives a signal indicating that an emissions test is in progress. When an emissions test is in progress, there will likely be a large carbon dioxide content in the gas in the sample cell 11. This results in a large signal in the carbon dioxide channel, channel 2 in this example. This signal, at the terminal P1-31 is applied to a comparator 114 where it is compared with a reference voltage REF1 to produce an appropriate digital signal when the comparator 114 indicates high carbon dioxide. Terminal $Y_2$ receives zero command signals from the host 92 and/or directly from the microprocessor 90. The microprocessor signal is developed on its port PA6 (as will be described below) and inverted by an inverter U7-3,4. This is a "ZERO REQUEST" signal that is applied directly to the terminal $Y_2$ when a switch 116 is closed. The terminal $Y_3$ is not used in the microprocessor program described below. It is provided in order to accommodate different numbers of channels. A three channel system is described below. A signal on the terminal $Y_3$ would be used if an optional single channel operation were programmed.

One of the causes of zero drift is variation of ambient temperature, which may cause changes in the source 13, the detectors 15-1, 15-2, 15-3 or the transmission of radiation between them. As will be explained in greater detail below, provision is made for entering the zeroing regime whenever there has been a drift in ambient temperature of more than 6° C. since the last zeroing. This requires a temperature measurement. In the illustrated embodiment, temperature is sensed by a thermistor 118, which is connected in a sort of bridge circuit including a series resistor 120, the DAC 21, a resistor 122, and a resistor 124. The thermistor 118 is connected to +15 v and the resistor 124 is connected to −15 v. The output of the bridge is taken from the junction of the resistors 122 and 124 and is compared to o or ground. The bridge is balanced when the output is o. This occurs when the DAC effectively complements the resistance of the thermistor 118. That is, if temperature changes change the resistance of the thermistor 118, the bridge is balanced when the DAC changes in complementary fashion. The state of the DAC at balance is thus a measure of temperature. The temperature measurement is effected through channel 3 of the demultiplexers 20 and 104 and the multiplexer 22. When channel 3 is energized by the control signals from the microprocessor 90, the microprocessor 90 operates as described above (and below) to place the DAC 21 in the condition that drives to 0 the voltage at the junction of the resistors 122 and 124, balancing the bridge. The microprocessor 90 includes a register that holds the digital signals from the microprocessor 90 to the DAC 21 at balance during any zeroing. The microprocessor compares subsequent digital signals at balance to the stored signals and flags a difference signifying a change of more than 6° C.

As will be explained further below in connection with the operation of the microprocessor 90, there are three microprocessor output signals in the preferred embodiment, READY on output port PA5, as inverted by an inverter U7-1, 2, ZERO REQUEST on output port PA6 as inverted by the inverter U7-3, 4 and PUMP & SOLENOID on output port PA7 as inverted by an inverter U7-5, 6. These signals may be indicated by respective LED circuits, indicated as optional in FIG. 4A. These signals are transmitted to the host 92. The host 92 responds to these signals by producing appropriate control signals for filling the sample cell 11. The sample cell is filled by a pump 126 through the inlet coupling 67. The filling gas is determined by a valve 128, which may be a solenoid operated spool valve, which selects between two input gases, the zero gas and the sample gas. In the course of calibration, a known gas of predetermined concentration is furnished as the sample gas; whereas, during measurement the gas being analyzed is furnished. The host operates the solenoid actuator of the valve 128 and the motor driving the pump 126 at such times as to effect the filling of the sample cell 11 with the appropriate gas.

The infrared gas analyzer shown in FIG. 1 will now be more fully described with respect to the software which controls the automatic zeroing of the channels. The software is stored in a ROM internal to the microprocessor 90 and controls the operations of the system and communications with the host 92. The system operation is shown in flow chart form in FIGS. 8–15 and a state-transition diagram of the operation of the control program is shown in FIGS. 6 and 7.

Figures 6, 7:
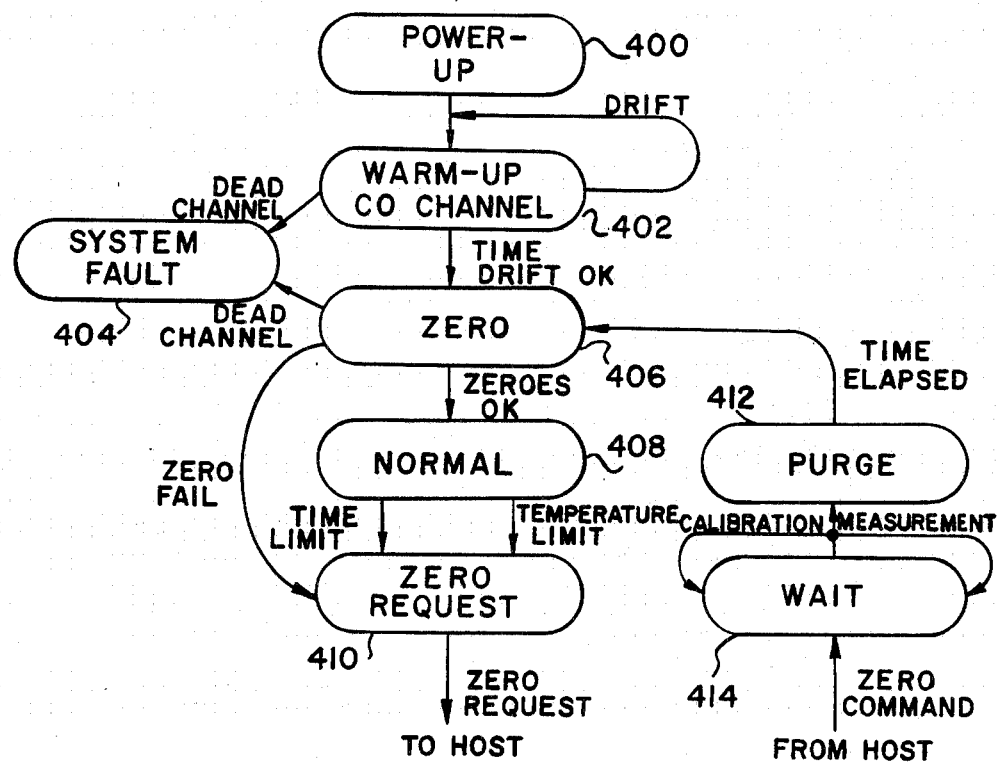
FIG. 6 is a pictorial representation of the transition between operational modes of the gas analyzer system illustrated in FIG. 1.
FIG. 7 is a state transition diagram illustrating the signal levels for the ready, pump & solenoid and zero request lines for the operational modes of the gas analyzer system illustrated in FIG. 1.

By reference to the state transition diagram of FIG. 6, it is seen that after a power-up mode 400, the first operation of the system is a warm-up mode 402. In the warm-up mode 402, the system waits through a warm-up interval. Afterwards, the CO channel (channel 1) is zeroed and measured against an offset after a drift delay. If the CO channel zero has drifted more than the offset, the system is not entirely warmed up and should be allowed to settle, and thus, the cycle is repeated until the drift is less than the offset. After the warm-up cycle is exited by a successful passage of the drift test, the mode will be changed to those modes comprising the basic operation of the system. The mode that begins basic operation is the zero mode 406 where all channels including the CO, HC, $CO_2$, and temperature channels are balanced or zeroed against references with a zero gas contained in the measuring or sample cell 11.

Once the zero mode 406 has been completed successfully, the system will make a transition into the normal mode 408. In the normal mode, measurements or analyses of the unknown gas mixture can be made by the host with the system maintaining its calibration. After warm-up mode 402 and zero mode 406, this is the main operational mode for the system, and most of the system time will be spent in the normal mode 408. However, for a number of predetermined conditions, the system is automatically zeroed through the zero mode 406 and passes through three other modes including a zero request mode 410, a wait mode 414, and a purge mode 412 to get there.

The zero request mode 410 is entered from either the zero mode 406 or the normal mode 408. The condition which switches the system from a zero mode 406 to a zero request mode 410 is an indication that one or more of the channels have failed to come to a zero condition. The zero request mode 410 is the first mode in a sequence which automatically attempts to rezero the channel which caused the request (actually all channels). When the system senses the zero fail condition, the zero request mode 410 is enabled and a zero request is generated on the zero request line either to the host 92 or back to the microprocessor 90 through a jumper (switch 116) to the zero command line ($Y_2$ of the demultiplexer 108). The conditions which switch the system from a normal mode 408 to a zero request mode 410 are the expiration of a predetermined time limit or the change of the ambient temperature greater than a predetermined limit. In the present embodiment, the time limit is 15 minutes and the temperature limit is ±6° C. different from the ambient temperature at which a particular channel was last zeroed. In response to the zero request mode, a zero request is made of the host 92, which returns a zero command, or the zero request is applied through the jumper 116 to the microprocessor 90, directly. Further, if the system is in the normal mode 408, the host can issue a zero command on its own.

In response to a zero command, either in answer to the zero request or from the host directly, the system enters a wait mode 414 where two conditions are tested. First, the system tests whether the $CO_2$ channel reading is greater than a predetermined limit. If this limit is exceeded, it is an indication that the system is performing an emissions test, and it would be inopportune to perform the zero operation. Therefore, the system will loop at the wait mode 414 until the $CO_2$ channel reading becomes less than the limit. Further, during an electronic calibration, the system should not be zeroed, and the wait mode 414 will be executed until an indication that a calibration is complete has been given.

If the signal in the $CO_2$ channel is not greater than the limit and the electronic calibration is not engaged, the system will go directly to a purge mode 412. The purge mode 412 is a timed mode where the pump and solenoid are turned on to fill the sample cell 11, insuring that the zero gas enters the cell and all remaining constituent gases of the last analysis are exhausted. After the time has expired for the purge mode 412, the system will cycle back to the zero mode 406 and continue the loop from there. Upon the zero mode 406 finding any dead channel for CO, HC, or $CO_2$, the system will enter a system fault mode 404 which causes an entire system shutdown. The system fault mode 404 is also entered upon the finding of a dead channel in the warm-up mode 402. The system fault mode 404 causes the microprocessor 90 to enter an infinite loop which can only be exited by a reset or power-down of the system.

The most common operation of the system is a cycling between the normal mode 408 and the zero mode 406 every 15 minutes because of a time limit. This is the auto-zero function of the system which uses the zero request mode 410, wait mode 414, and purge mode 412 to assist in the cycle.

FIG. 7 illustrates the states of the three communication and status lines, ready, zero request, and pump & solenoid for each of the system modes. The zero request line is only true during the zero request mode 410 when requesting the host 92 to generate a zero command. The ready status line is only true during the normal mode 408 when the host can perform calibrated measurements. During the zero request mode 410 and the wait mode 414, an indicator is set to blink to alert a subsequent ready state. The pump and solenoid line is true during the modes of warm-up 402, zero 406, and purge 412 to request the host to fill the cell 11 with a zero gas.

Figure 8A:
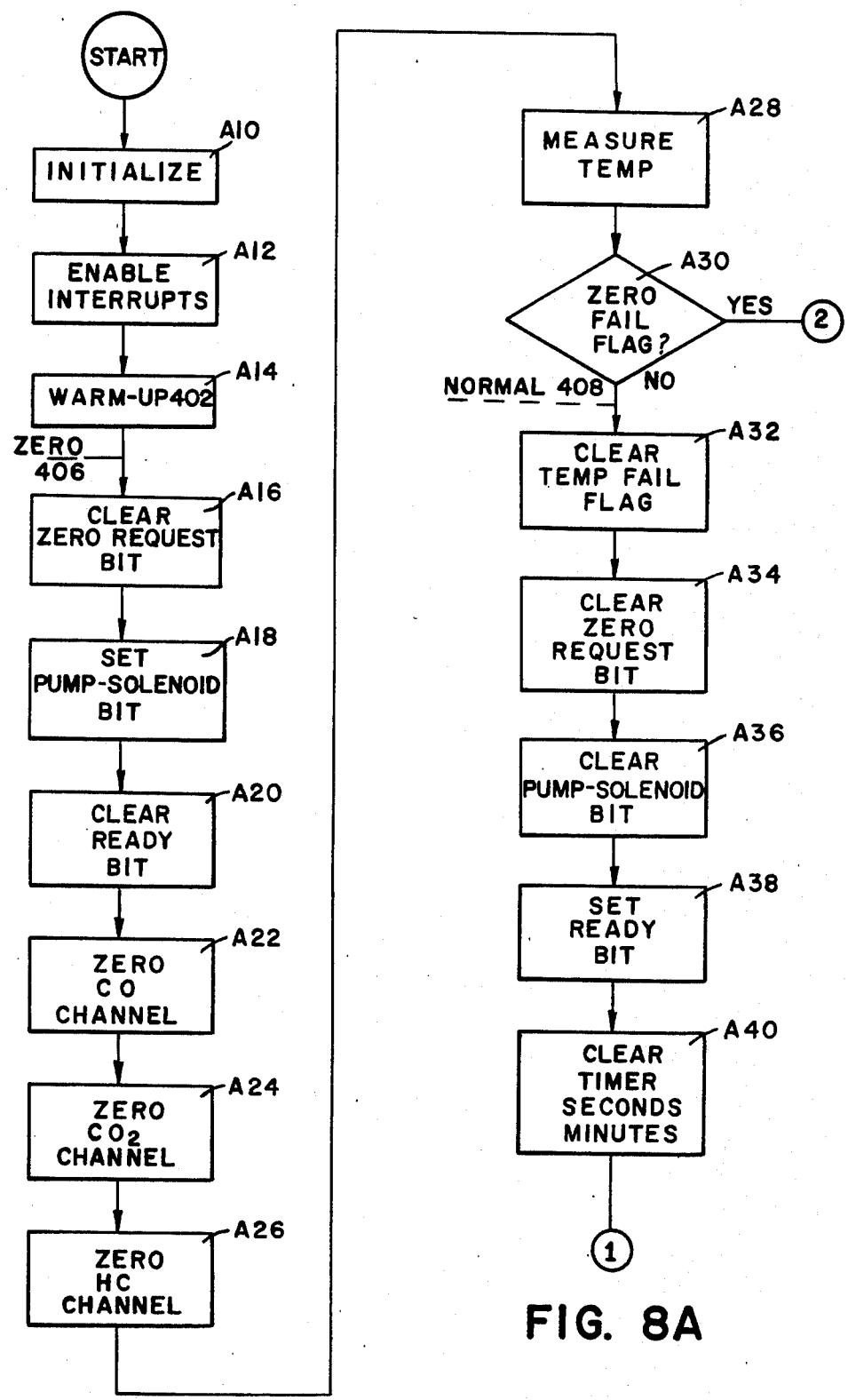
FIGS. 8A–8C are a detailed flow chart of the software program controlling the processor of the gas analyzer system illustrated in FIG. 4.
Figure 8B:
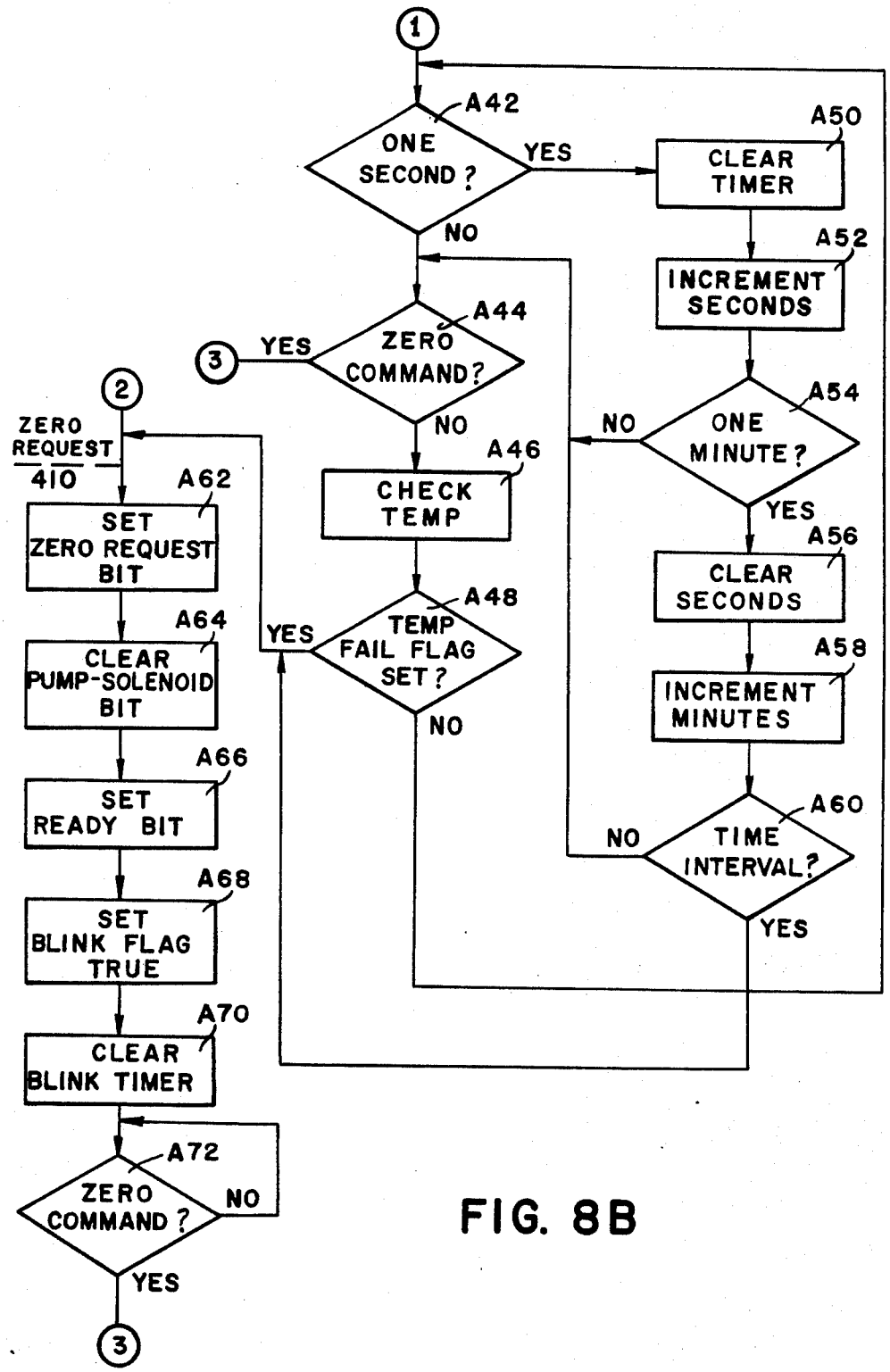
Figure 8C:
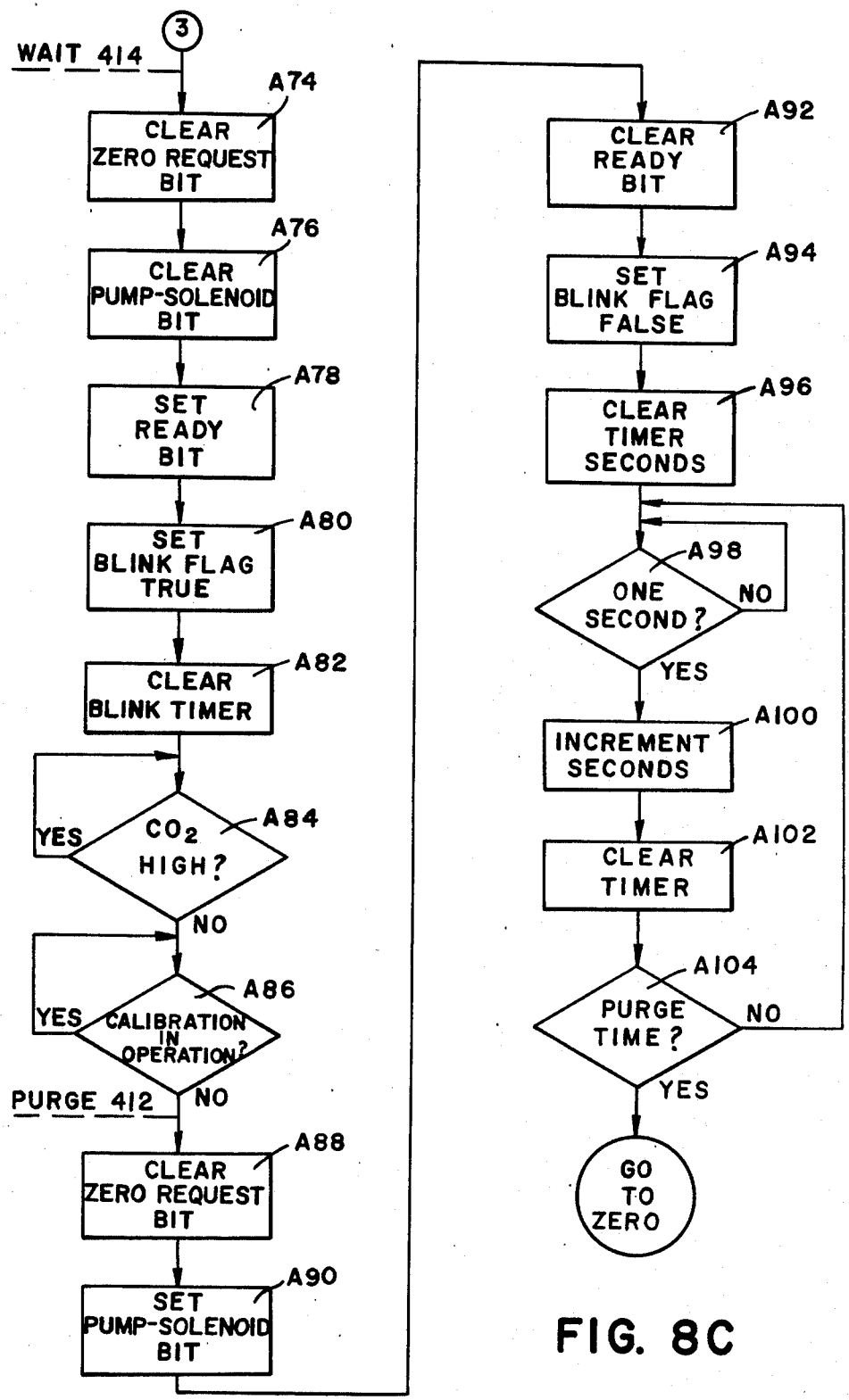
Figure 9:
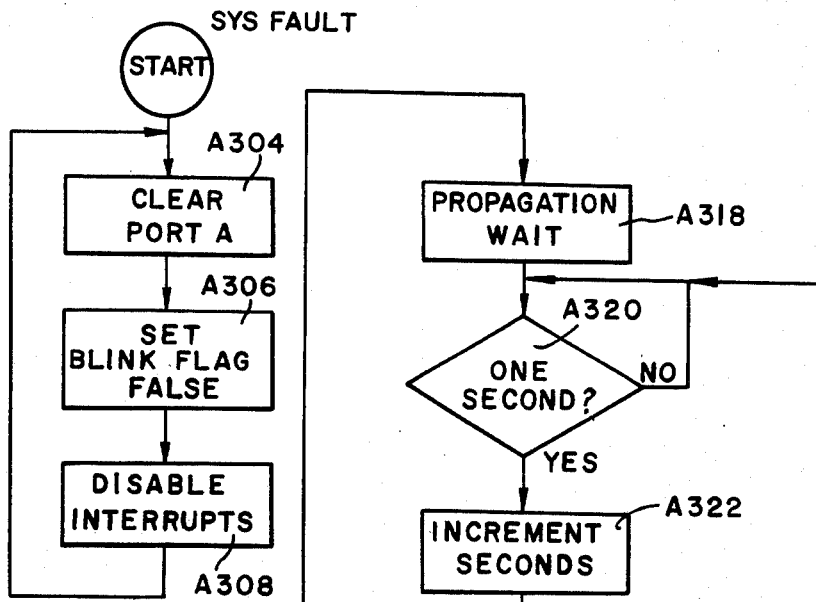
FIG. 9 is a detailed flow chart of the subroutine SYS FAULT called by the system program illustrated in FIGS. 8A–8C.

These functional modes are implemented by a program stored in the microprocessor 90 for which a system flow chart is shown in FIGS. 8A-8C. The program begins the operation of the system by initializing particular constants in the microprocessor 90 in block A10. Particularly, the port data directions and initial port patterns for port A, port B, and port C are initialized with the predetermined values. Next in the initialization step, a number of pointers are stored to provide address references to particular points in the program. The initialization then clears particular variables used in the operation of the program, and starts the hardware timer on the microprocessor 90. After initialization, the program enables the interrupts in block A12 to allow an interrupt routine to act as a foreground routine while the following program executes in background. The hardware timer will cause a real time interrupt and a transfer of control from this main routine to the interrupt routine every 10 milliseconds.

Figure 10A:
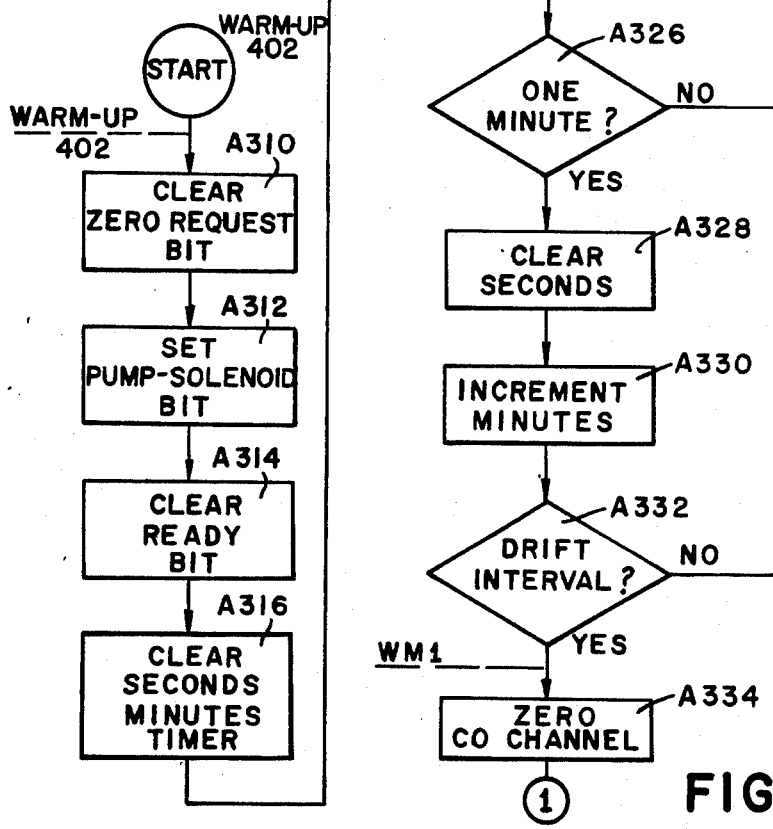
FIGS. 10A, 10B are a detailed flow chart of the subroutine WARM UP called by the system program illustrated in FIGS. 8A–8C.
Figure 10B:
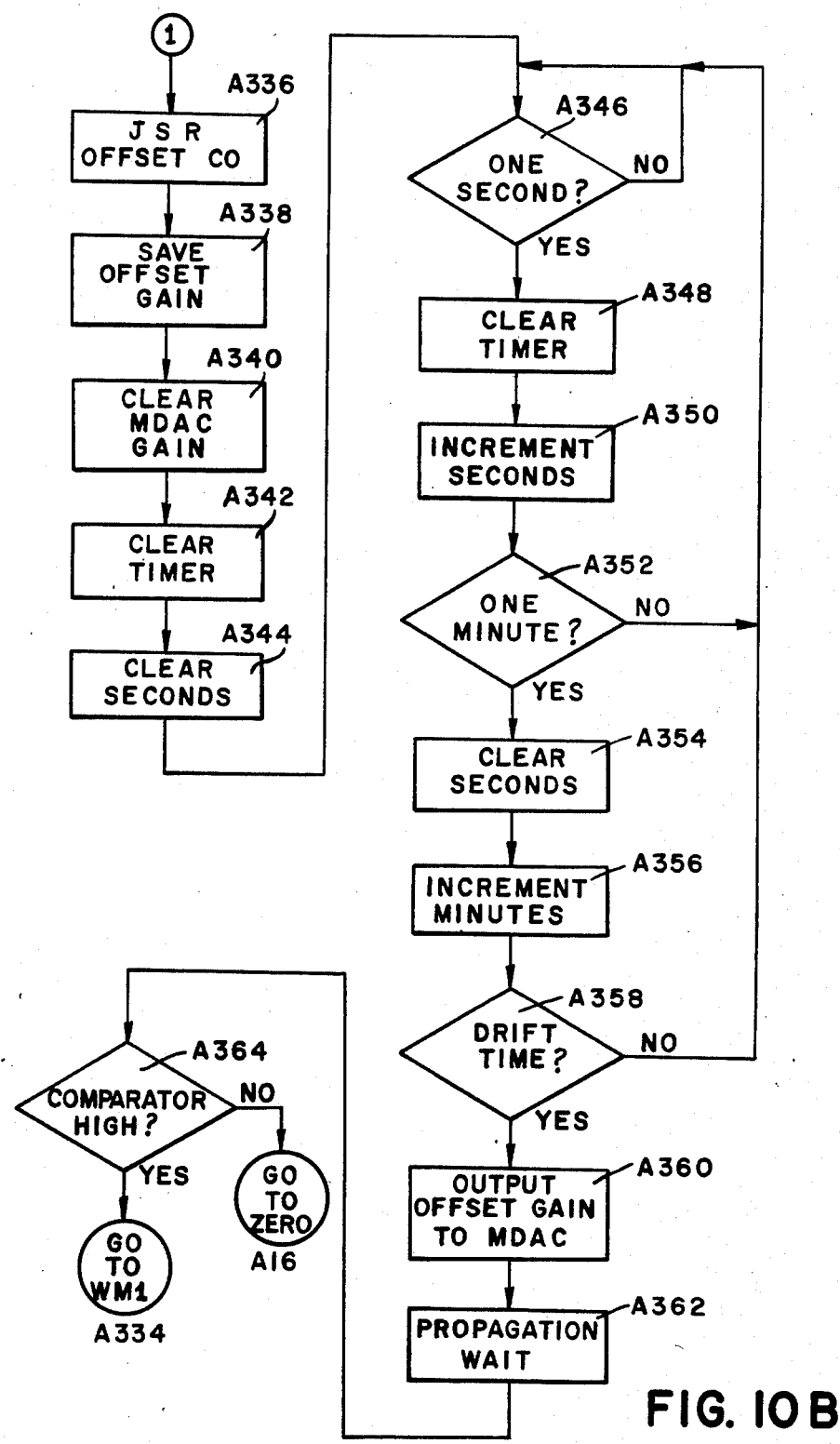

In the next block A14, a warm-up routine is executed which will be more fully described hereinafter by reference to FIGS. 10A and 10B. Basically, the warm-up routine delays a specified period of time and then zeros the CO channel and determines whether the channel is drifting. As soon as the system is stable, the program continues to block A16 where the start of the zero mode 406 is located. The RAM mapped images of the output lines PA5, PA7, and PA5 of the microprocessor 90 corresponding to the zero request bit, pump and solenoid bit, and ready bit, respectively, have their states set according to the mode. Because the system is in the zero mode, the zero request bit should be cleared, the pump and solenoid bit should be set, and the ready bit should be cleared. These operations are performed in blocks A16-A20. The setting of the pump and solenoid bit will request that the host 92 turn on the pump 126 and switch the solenoid valve 128 to the zero gas side such that the auto-zeroing of the system can be accomplished. Next in block A22, the CO channel is zeroed by calling a subroutine SAR which will be more fully explained hereinafter. In block A24 the $CO_2$ channel is zeroed in the same manner by again calling subroutine SAR. Likewise in block A26, the HC channel is zeroed by calling the subroutine SAR.

The subroutine SAR basically determines the MDAC gain value which will cause the comparison of the channel output and the reference voltage to be zero. If the subroutine SAR cannot zero a particular channel, it will set a flag which is termed the zero fail flag. After all three channels have been zeroed, in block A28 the system will measure the temperature with a subroutine SAR TEMP which determines the ambient temperature at the time of the auto-zero operation. Next in block A30, the zero fail flag is tested to determine whether or not any of the channels have not been properly zeroed. If the zero fail flag is not set, then the program advances to the normal mode 408 which starts at block A32. Otherwise, the program will branch to block A62 (FIG. 8B), which is the start of the zero request mode 410.

In the normal mode 408, the program clears the temperature fail flag in block A32 before resetting the three output bits for output lines PA5, PA6, and PA7. The zero request bit is cleared in block A34, the pump & solenoid bit is cleared in block A36, and the ready bit is set in block A38. These operations alert the host with the ready line that a measurement may now be made and that the auto-zeroing has been concluded. The ready line indicates that all channels have been successfully zeroed and that the system is prepared to accurately measure the constituent gases within the cell 11. The pump and solenoid bit is cleared to move the solenoid valve 128 to permit the unknown gas to enter the cell 11 and to allow the host 92 to control the pump 126.

Next in block A40, the hardware timer for the normal mode 408 is reset. This is accomplished by clearing the hardware timer location, the seconds location, and the minutes location. These locations are used in a timing loop illustrated by block A42 and blocks A50–A60. The timing loop counts the time interval between the auto-zero operations in 10 millisecond increments.

In block A42 a test is performed to determine if enough 10 millisecond increments have been accumulated to equal one second. If not, the program drops through to a number of tests in blocks A44, A46, and A48. In the first test, block A44, the program determines whether or not the host has generated a zero command to the microprocessor 90 via input $Y_2$ of the demultiplexer 108 and pin PA4 of the microprocessor. If the test in block A44 is affirmative, then the program will branch to block A74 (FIG. 8C) where the wait mode 414 is entered. However, if there is no zero command, then the program will measure the temperature change at that particular point in time in block A46 by calling the subroutine CHECK TEMP. The temperature change is measured in this routine by comparing the gain corresponding to the current temperature with the stored gain corresponding to the temperature at the last auto-zero operation ± an offset. The comparator input on pin PA3 will then indicate a change in temperature. If the change in temperature is greater than ±6° C., then the program will set the temperature fail flag. This is an indication that the temperature has changed more than the range allowed within the last 15 minutes, the time limit interval.

Therefore, in block A48, if the temperature fail flag has been set, the program will branch to block A62 which is the start of the zero request mode 410. However, if the test in block A48 is negative indicating that there was no zero command and the temperature is still within range, then the program loops back to block A42 to continue executing the timer loop. At the end of every second, the test in block A42 will be affirmatively passed and a loop consisting of blocks A50, A52, and A54 executed. In block A50 the timer location is cleared and in block A52 the location labelled seconds is incremented. Thereafter, the program tests in block A54 whether one minute has expired by comparing seconds with a constant 60. Thus, this loop counts in increments of one second to one minute and then clears the location labelled seconds in block A56 and increments the location labelled minutes in block A58. The test in block A60 is executed to determine if the number of minutes counted by the loop is equal to the time interval, which in our example is 15 minutes. If not, the loop repeats by executing the blocks A44, A46, and A48 before incrementing the timer counts. After the time interval has expired, the program will affirmatively branch from block A60 to block A62, which is the beginning of the zero request mode 410.

Thus, there are three ways to exit from the normal mode loop, namely a zero command, a temperature fail flag, and the time out of the auto-zero interval. On either the temperature drift or the time limit conditions, the program will sequence from the normal mode 408 to block A62 which begins a zero request mode.

In block A62, the zero request bit is set while in block A64 the pump & solenoid bit is cleared, and in block A66 the ready bit is set. Setting the zero request bit requests the host to reply with a zero command for auto-zeroing. In this manner the system signals the host 92 that it is ready to do auto-zeroing. With the jumper 116 in place, the zero request can directly generate the zero command such that this path will automatically put the microprocessor 90 into the zero mode 406. In blocks A68 and A70, the blink flag is set true, and the blink timer location is cleared. This will allow the interrupt routine to determine whether the ready line should be toggled at half second intervals, with such operation taking place in that routine. After these operations have been concluded, the program loops at block A72 until a zero command is recognized at pin PA4 of the microprocessor 90.

When the zero command is sensed, it transfers the program to block A74 and the beginning of the wait mode 414. In this mode, the three reference lines are set to the particular states of the mode such that the zero request bit is cleared in block A74, the pump & solenoid bit is cleared in block A76, and the ready bit is set in block A78. In block A80 and block A82 the blink flag is set to true, and the blink timer is cleared. These are the same states as for the zero request mode except that the zero request line has been cleared to indicate that the request has been answered.

Next in blocks A84 and A86, the conditions for the wait mode 414 are tested. In block A84 the multiplexer 108 input $Y_1$ is tested to determine whether the output of the comparator 114 is at a high logic level. This is done by sampling pin PA4 of the microprocessor 90 during the switching of the multiplexer 108 to that channel. The input to the comparator 114 is from the output of the $CO_2$ channel and is compared against a reference REF1 developed at the node of two resistors R23 and R24. If $CO_2$ is at a higher concentration than a certain percentage, in the preferred embodiment 1.5%, then the output of the comparator 114 is at a high logic level, and the test is affirmatively passed.

A $CO_2$ concentration of this amount or higher indicates that the system is performing an emissions test and that the auto-zero should wait until the analysis is over. This wait occurs even though there has been a zero command either from the host or in reply to the zero request from the microprocessor 90. When the voltage indicating the $CO_2$ concentration drops below the reference REF1, the loop is exited to block A86 where the condition of an electronic calibration is tested for.

This operation is tested by sampling pin PA4 of the microprocessor 90 when the multiplexer 108 is selecting input $Y_0$. The input to the multiplexer channel $Y_0$ at that time is the output of comparator 112 which includes inputs through diodes 110 which are connected to the electronic calibration resistors 102-1, 102-2, and 102-3 (FIG. 5). When any one of these calibration resistors is not grounded during electronic calibration, a negative signal is applied through the wired-OR diode array 110 to the inverting input of the comparator-amplifier 112. This causes the comparator-amplifier to produce a high level output which is transmitted to pin PA4 of the microprocessor 90 and which is read during the interrupt routine for the front panel. As long as the calibration operation continues on any channel, the program will loop in block A86 such that the auto-zero operation will not occur.

After both of the conditions that maintain the system in the wait mode 414 are cleared, the negative paths of blocks A84 and A86 transfer the system into the purge mode 412 beginning at block A88. The purge mode is a timing loop to insure that the pump 126 and solenoid value 28 operate at least a predetermined amount of time, called the purge time, before the auto-zero operation is started. The operation purges the cell 11 of residual analysis gas and insures a sufficient quantity of the zero gas has been pumped into the cell 11. In blocks A88–A92 the control bits for the zero request, the pump and solenoid, and the ready lines are set according to the state table. The zero request bit is cleared in block A88, the pump and solenoid bit is set in block A90, and the ready bit is cleared in block A92. To indicate that the system is not in a ready state, the blink flag is set to false in block A94.

Thereafter, the purge timer loop, blocks A96–A104, is entered. In block A96 the timer is cleared and the seconds location cleared. The program then loops at block A98 until one second has elapsed on the timer. The program then increments the seconds location in block A100, clears the timer, and compares the seconds location with the purge time in block A104. If the purge time has not elapsed, the negative branch from block A104 begins the loop once again at block A98. Once the purge time, 30 seconds, has elapsed, the affirmative branch of block A104 transfers the program back to the zero mode 404 at A16.

The warm-up mode 402 will now be more particularly described with reference to FIGS. 10A and 10B. The warm-up mode allows a set time after the power is turned on where the cell warms up such that drift and transient readings are not taken in the auto-zeroing. In blocks A310, A312, and A314 the system status bits for the request line, pump and solenoid line, and ready line are determined. These three blocks set the pump and solenoid bit, and clear the zero request bit and ready bit. Thus, the pump and solenoid bit is set to produce a condition where zero gas is pumped into the cell and the ready signal to the host is cleared indicating a busy condition. A warm-up delay loop is then entered where for 15 minutes the system idles waiting for the timer to complete the interval. In block A316 the location seconds, minutes, and timer are cleared and the propagation wait subroutine executed in block A318. Thereafter, the timer is compared against one second in block A320. Once one second has elapsed, the program continues by incrementing the location seconds in block A322 and by clearing the location timer in block A324. Next, the location seconds is tested against one minute (60 seconds) in block A326. If one minute has not elapsed, then the program loops back to block A320 to continue to count seconds. Otherwise, in block A328 the location seconds is cleared and in block A330 the location minutes is incremented. Thereafter, each minute the program will advance through the test in block A326 and go through the test in block A332 to determine if the warm-up interval (15 minutes) has elapsed. If not, the beginning of the loop is branched to by a transfer of control to block A320.

Once the warm-up interval has elapsed, the program advances to location WM1 where the routine SAR is called to zero the CO channel in block A334. If the CO channel cannot be zeroed or fails the zero offset test, then either the zero fail flag will be set or the system will enter the system fault routine. However, if a valid zeroing of the CO channel is accomplished, then the program will progress to the next block A336 where the subroutine OFFSET CO is executed. This subroutine takes the MDAC gain determined in block A334 and subtracts an offset from it to determine an offset gain used for the drift test. If the CO channel is stable, then the original CO channel gain minus the offset will not cause the comparator 106 to make a transition. This offset test gain is saved in block A338 and the locations in which the MDAC gain zeroed is stored is cleared in block A340 during a drift interval.

A timing loop consisting of blocks A342–A360 is then entered to delay the program for the drift interval time. The timing loop initiates by clearing the timer and clearing the location seconds in blocks A342 and A344, respectively. Seconds are tested at block A346, and each one second interval causes a clearing of the timer and an incrementing of the location seconds in block A348 and A350, respectively. Minutes are tested for by comparing the seconds location to 60 in block A352 and then clearing the seconds location and incrementing the minutes location in blocks A354 and A356, respectively, upon the passage of each minute. The minutes location is then compared to a drift time constant in block A360 to finally exit the loop when the drift time has elapsed.

In block A360 the offset gain is output to the MDAC and the propagation wait routine called in block A362. In block A364 the comparator 106 is tested to determine whether the output has changed more than a particular amount during the drift time interval. If the output of the comparator 106 as tested for in block A364 is high, this condition indicates that the system has drifted. An affirmative response to the test causes the program to cycle back to the address WM1 where the CO channel is again zeroed starting at block A334. The loop continues until the channel is stable enough such that it does not drift more than the offset over the drift time interval. At that point the warm-up mode 402 is exited by the negative branch from block A366 to the address zero (FIG. 8A) to begin the zero mode 406.

Figures 12, 13:
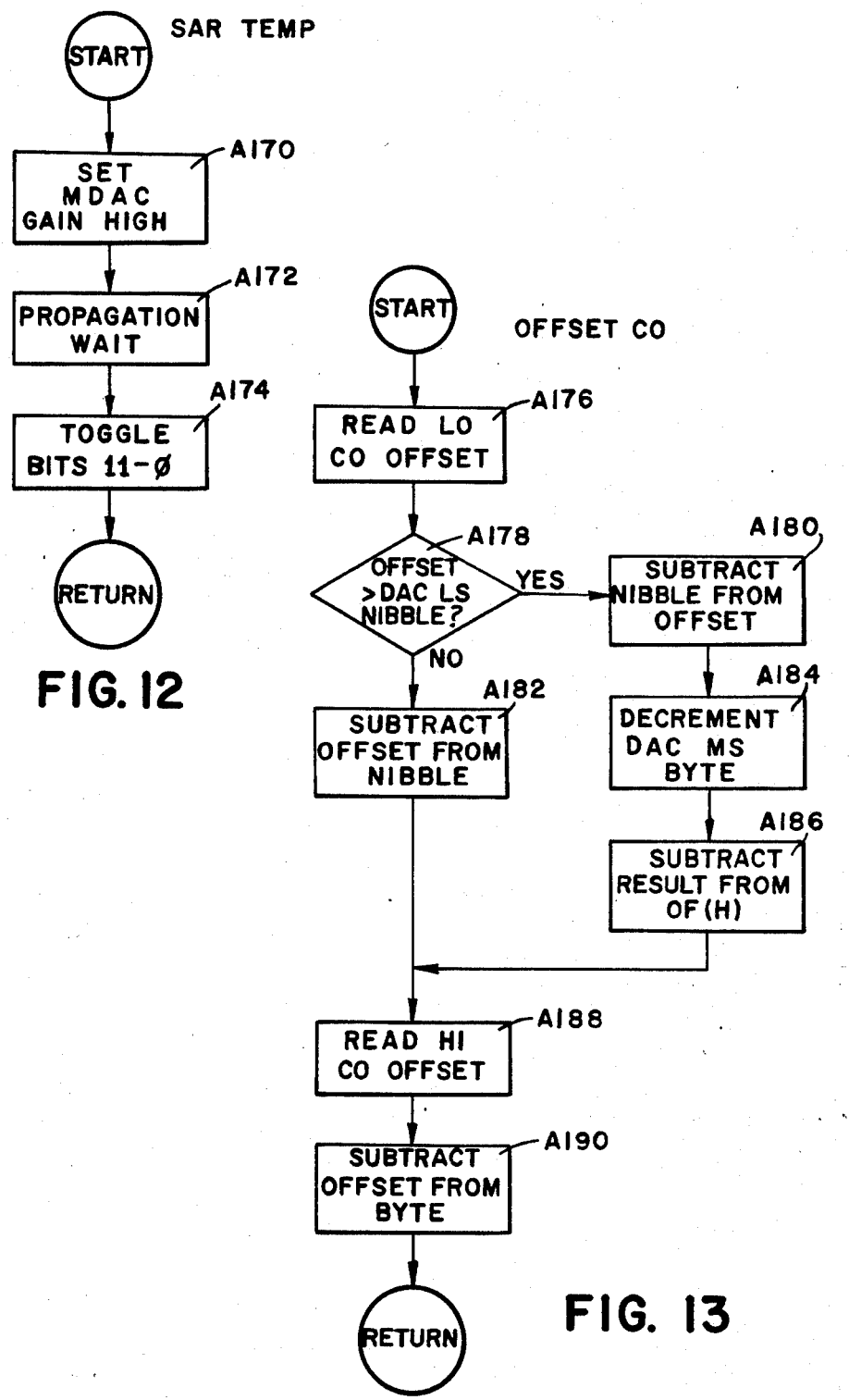
FIG. 12 is a detailed flow chart of the subroutine SAR TEMP called by the system program illustrated in FIGS. 8A–8C.
FIG. 13 is a detailed flow chart of the subroutine OFFSET CO called by the subroutine WARM UP illustrated in FIGS. 10A, 10B.

The subroutine OFFSET CO is illustrated in FIG. 13. The purpose of the OFFSET CO routine is to subtract an offset from the MDAC gain used to zero the CO channel to determine if the system is still drifting during the warm-up mode 402. In block A176 the low byte of the CO offset is read and compared in block A178 against the least significant nibble of the MDAC gain. Depending upon which is larger, the nibble is subtracted from the offset in block A180, or the offset is subtracted from the nibble in block A182. If the nibble is subtracted from the offset, then a borrow from the most significant byte of the MDAC gain must be accomplished in block A184 and the most significant byte decremented. The result of the subtraction in block A180 is then subtracted from a full least significant byte increment (OF) in block A186, the difference being equivalent to the subtraction of the offset from the nibble after borrowing. Next the high byte of the CO offset is read in block A188 and then subtracted from the most significant byte of the MDAC value in block A190. The routine then returns to the warm-up mode program from which it was called.

Figure 11A:
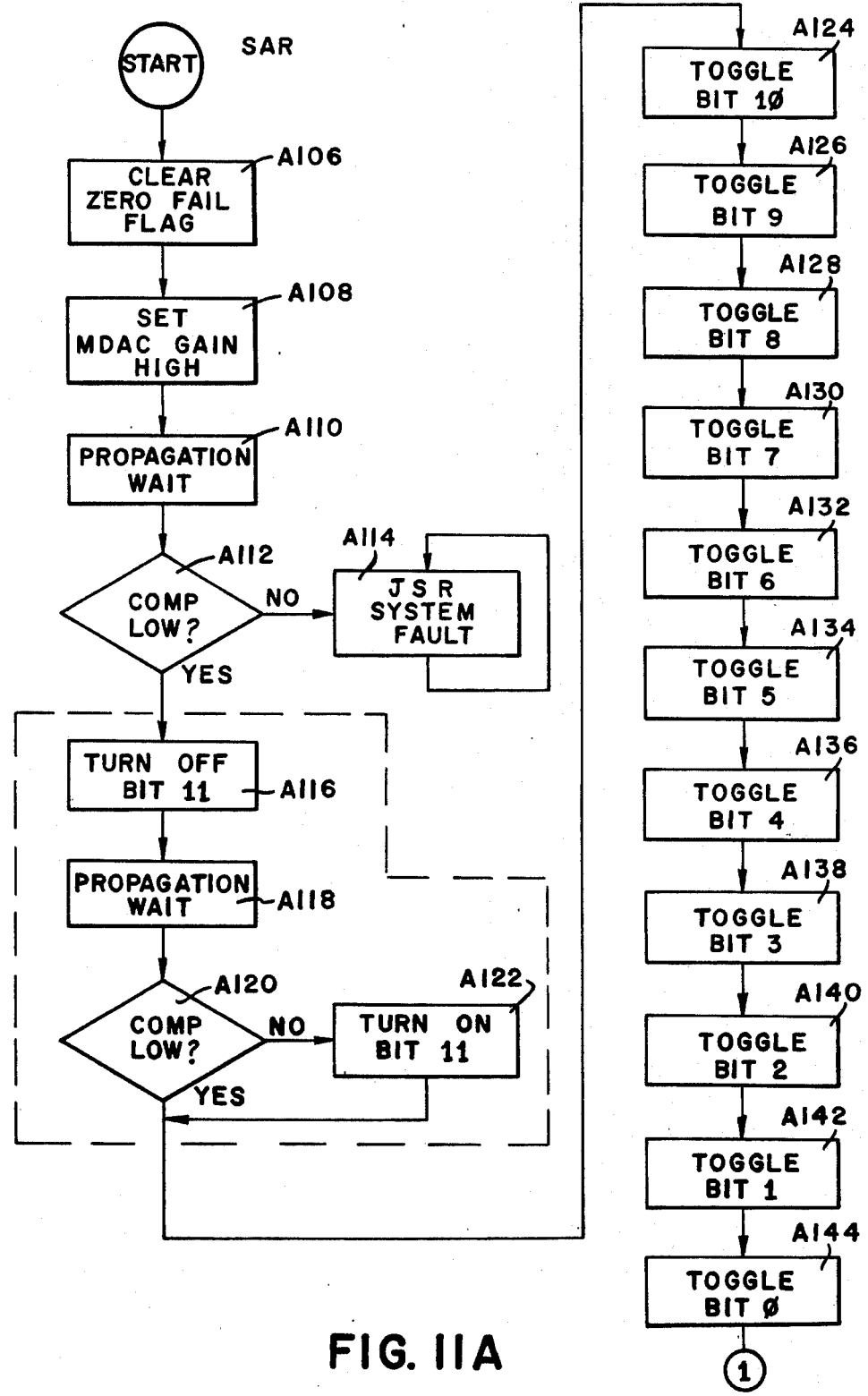
FIGS. 11A, 11B are a detailed flow chart of the subroutine SAR called by the system program illustrated in FIGS. 8A–8C.
Figure 11B:
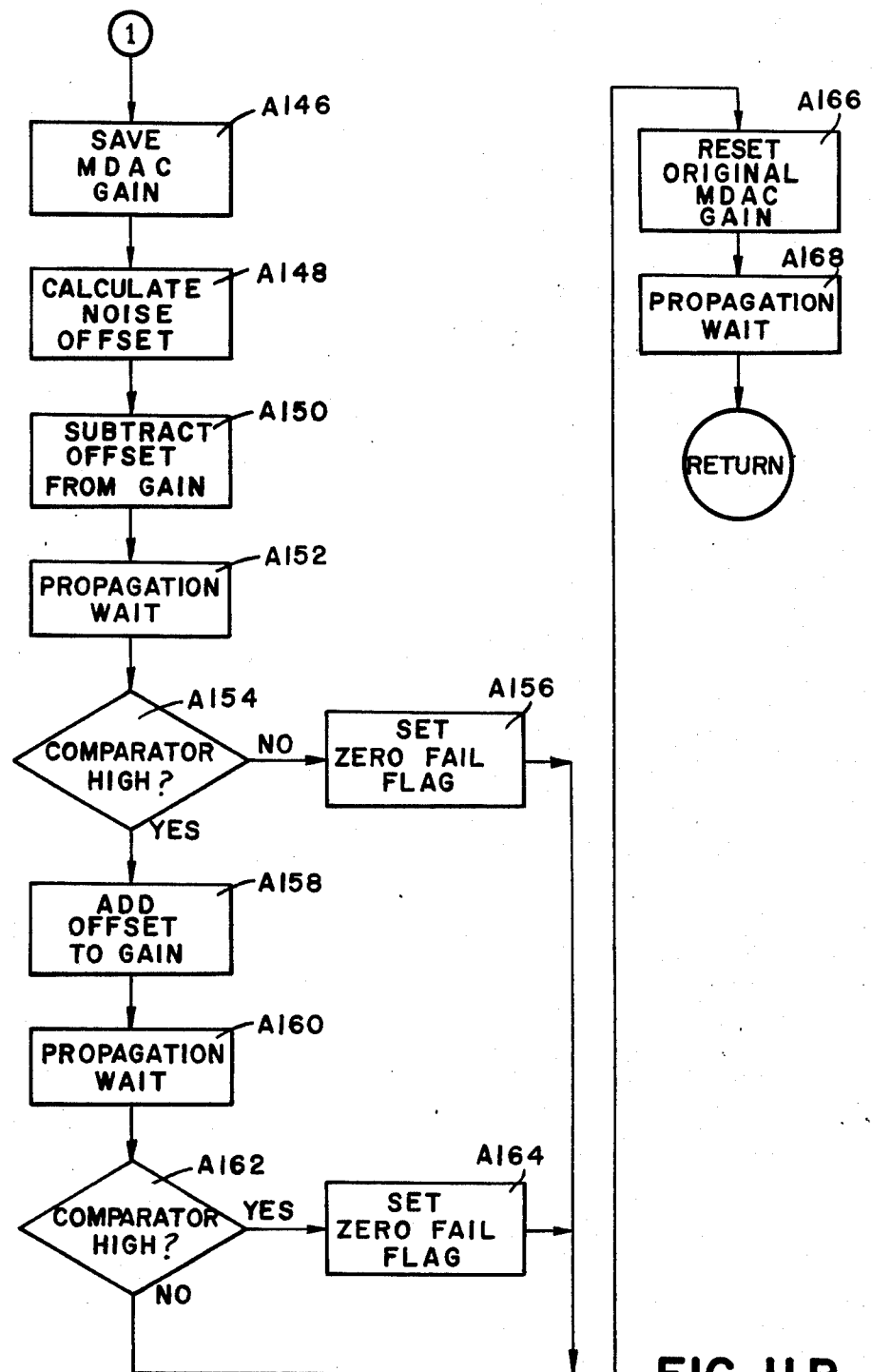

The subroutine SAR, more fully detailed in FIGS. 11A and 11B, is the routine used to zero a channel by successively approximating the digital gain for the MDAC 21 which will cause a zero condition at the comparator 106. The program begins in block A106 by clearing the zero fail flag which will be later used as an indication that the channel failed the zeroing operation if set. Next in block A108, the gain of the MDAC 21 is set to 100% by outputting a 12-bit word of digital ones (FFF) on port pins PC0–PC3, PB0–PB7 of the microprocessor 90. The program in block A110 enters a propagation wait subroutine so that the change in gain has time to propagate through the multiplexer 22, sample and hold circuits, and span amplifiers 23-1, 23-2, 23-3 to the comparator 106. In block A112 the program determines after the wait if the comparator is low. When the MDAC 21 is programmed with the highest gain value (FFF) this should bring the output of the comparator 106 low. If not, the channel cannot be zeroed and the absence of low comparator signal will be taken as a dead channel with the program branching to a system fault subroutine SYS FAULT at block A114.

The system fault subroutine SYS FAULT performs certain system shut down functions and then enters an infinite loop in the system fault mode 404. Once a dead channel is detected in this manner, the only methods of exiting the system fault mode infinite loop are either to reset the microprocessor 90 or power-down and power-up the system. The system fault subroutine SYS FAULT is illustrated as a detailed flow chart in FIG. 9. The system fault subroutine SYS FAULT is a infinite loop which is entered when the channel output of any of the channels cannot be made to produce a low output state on the comparator 106 even with the highest gain. This indicates that the channel is dead, i.e., there is some broken connection or inactive sensor in the input circuitry such that the system cannot measure the input from that particular channel. In block A304 the program clears port A essentially zeroing pins PA5, PA6, and PA7 to indicate the system fault mode 404. In block A306 the blink flag is set to false to disable any other setting of the ready line, and finally, in block A308 the interrupts are disabled. The microprocessor 90 then enters an infinite loop where a branch is made back to block A304 and continues in this loop until the microprocessor is powered down or externally reset by a switch.

Returning to the subroutine SAR (FIG. 11A), if the comparator 106 is determined in block A112 to be low, the system enters a toggle operation where the most significant bit (bit 11) to the MDAC 21 is turned off in block A116. The propagation wait subroutine is then entered in block A118 to allow the change in gain to propagate to the comparator 106. The comparator 106 is then read in block A120 by sampling pin PA3 and determining whether the comparator has remained low. If the comparator 106 has not remained low, the condition indicates that not enough gain is being applied to the MDAC 21 to zero the channel, and, therefore, the most significant bit is again turned on in block A122. If the comparator 106 does not remain low, the gain that needs to be applied to the MDAC 21 to zero the channel is greater than the most significant bit. However, if the comparator 106 remains low, this indicates that there is still too much gain but the gain necessary to zero the channel is less than the most significant bit (800H) and it is left off.

Thereafter, a successive approximation of the MDAC gain needed to zero the comparator 106 is determined by toggling each bit after the most significant bit in succession. Blocks A124-A144 toggle bits 10-0 OFF in succession and, similar to the previous case, either leave them off if the comparator 106 remains low or turn them back on if the comparator goes to a high state. The MDAC gain is found in this manner to zero the channel by successive approximations to a resolution of 12-bits and is thereafter saved in block A146.

Next, the MDAC gain which has been determined is used to calculate a noise margin in block A148. The noise margin is determined as 1/256th of the original MDAC gain which zeros the channel. This is the amount by which the signal may change when the channel is measured but still be considered to be zeroed. To determine if there is noise on the channel greater than this margin, the offset calculated is subtracted from the derived MDAC gain in block A150. The new gain (MDAC (ZERO)−OFFSET) is then applied to the MDAC 21 and allowed to propagate to the comparator 106 while the system waits in block A152. The comparator 106 is then read in block A154 to determine if comparator output is at a high value. If the comparator 106 does not make a transition to a high value when the offset is subtracted, then the zero gain was not calculated sufficiently accurately and the negative branch of block A154 transfers the program to block A156 where the zero fail flag is set.

If the system passes the first test, then in block A158 the gain derived from zeroing the channel is added to the offset. That new gain (MDAC (ZERO)+OFFSET) is then applied to the MDAC 21, and the system waits until the changes of the signal propagates through to the comparator 106 by calling the subroutine propagation wait in block A160. The comparator 106 is then read to determine if it is at a high logic level in block A162. If the comparator has not toggled to a low value with the addition of the offset, the MDAC gain which was derived will not zero the channel and, therefore, in block A164 the zero fail flag is again set.

After exiting from block A156, A162 or A164 the program continues at block A166 where the original MDAC gain is reset for the channel and the propagation wait routine is entered in block A168. If the tests are all passed, then that MDAC gain derived from the successive approximations will be used in the normal mode 408 for subsequent analysis readings of that channel. However, if the zero fail flag is set, then when the program returns from the SAR subroutine, the program in the zero mode 406 will branch to the zero request mode 410 to again request zeroing and a determination if the noisy channel can be zeroed.

The successive approximation routine for measuring the temperature will now be more fully explained with respect to FIG. 12. The temperature measurement subroutine labeled SAR TEMP begins in block A170 by setting the MDAC gain to its highest value (FFF). The system then waits for the propagation delay in block A172 so that the change in gain is allowed to change the output of comparator 106. Next in block A174, similar to the successive approximation routine for zeroing each channel, bits 11-0 are toggled to successively approximate the gain which balances the two legs of the bridge comprising the fixed reference voltages +15 V, and reference resistors 120, 122, 124 and the thermistor 118. After this value has been found, it is stored for further use as a reference temperature when the normal mode 408 is entered.

Figure 14:
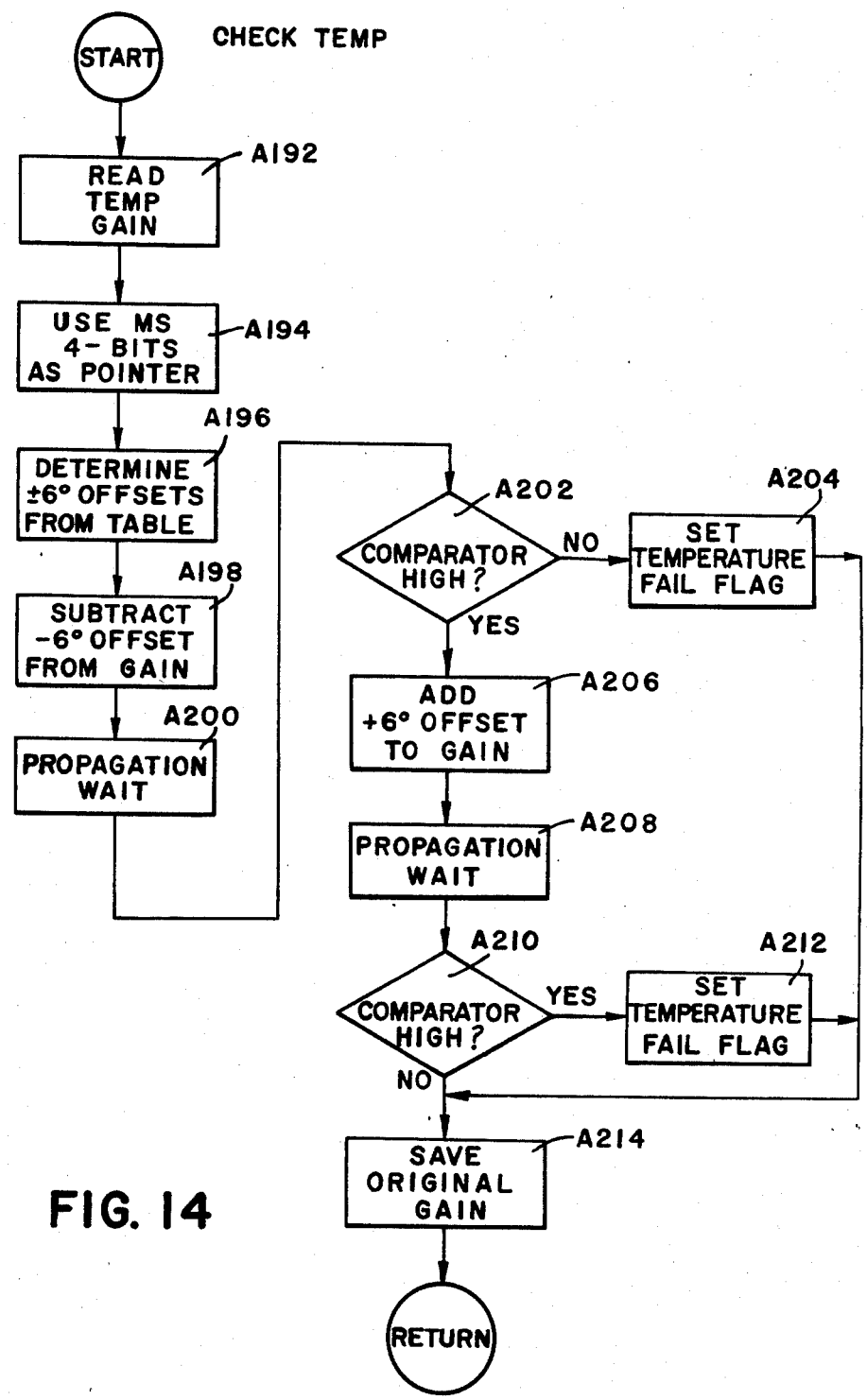
FIG. 14 is a detailed flow chart of the subroutine CHECK TEMP called by the system program illustrated in FIGS. 8A–8C.

The subroutine CHECK TEMP will now be more fully explained with respect to FIG. 14. In block A192 the MDAC gain which caused a zero for the temperature channel is read from memory. The most significant 4-bits of that MDAC gain word are used to determine one of sixteen pointer values in block A194. These pointer values are applied to high and low temperature tables from which offset values are derived. The offset value is representative of a change of ±6° C. from the original temperature value and indicated by the MDAC gain. Because the thermistor 118 and temperature versus voltage characteristics of the loop gain are nonlinear, this table look up allows the correct offset value from any temperature over the range of operation of the system to be determined for an accurate ±6° C. The gain offset is then subtracted from the original MDAC gain in block A198 and that new gain (MDAC (TEMP ZERO)−(TEMP−6° OFFSET)) applied to the MDAC 21. The propagation wait subroutine is entered in block A200 and thereafter the comparator 106 tested in block A202.

If the comparator 106 is at a high logic level, it indicates that the present temperature is higher than a temperature −6° C. from the original temperature. However, if the comparator is not high, then the temperature has changed more than 6° C. in the negative direction, and thus, the temperature fail flag will be set in block A204. If the first temperature offset test is passed, then the affirmative branch from block A202 continues the program at block A206 where the +6° C. offset is added to the original MDAC temperature gain. This new gain (MDAC (TEMP ZERO)+(TEMP+6° OFFSET)) is applied to the MDAC 21 and the system enters the propagation wait routine in block A208. The comparator 106 again is tested to determine the state level of its output. A low output indicates that the temperature has not changed in the positive direction by more than 6° C. since the temperature channel was measured during the zero mode. Therefore, the original MDAC temperature gain is saved in block A214, and the subroutine returns from where it was called. However, if the comparator 106 is high, then in block A212 the temperature fail flag is set indicating that the present temperature is outside of the offset range in the positive direction. If the temperature fail flag is set in either block A204 or A212, then the system will loop back from block A48 to the zero request mode 410 to request an auto-zero of all channels.

Figure 15A:
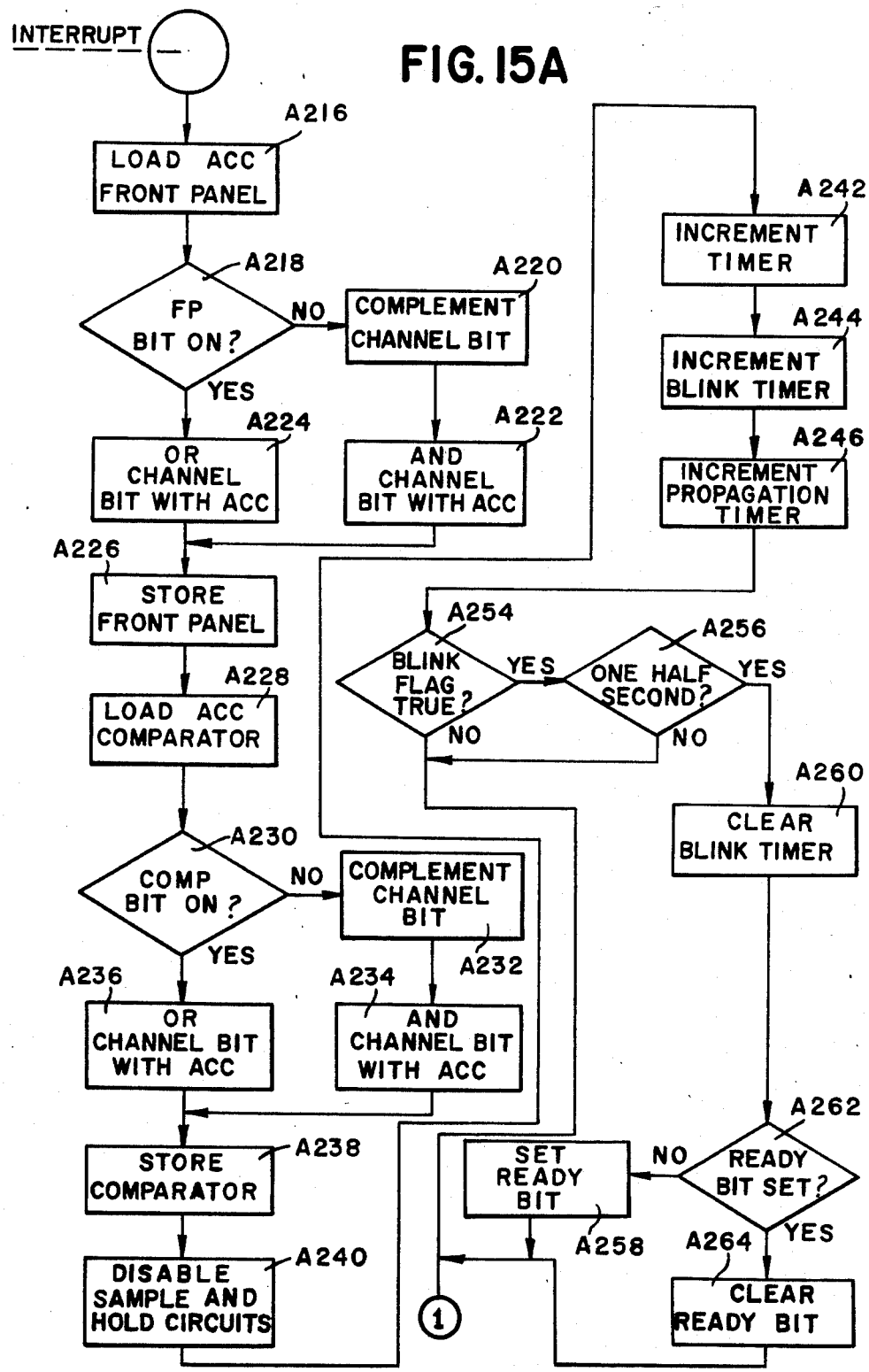
FIGS. 15A, 15B are a detailed flow chart of the program INTERRUPT which is executed in response to a timer interrupt in conjunction with the system program illustrated in FIGS. 8A–8C.
Figure 15B:
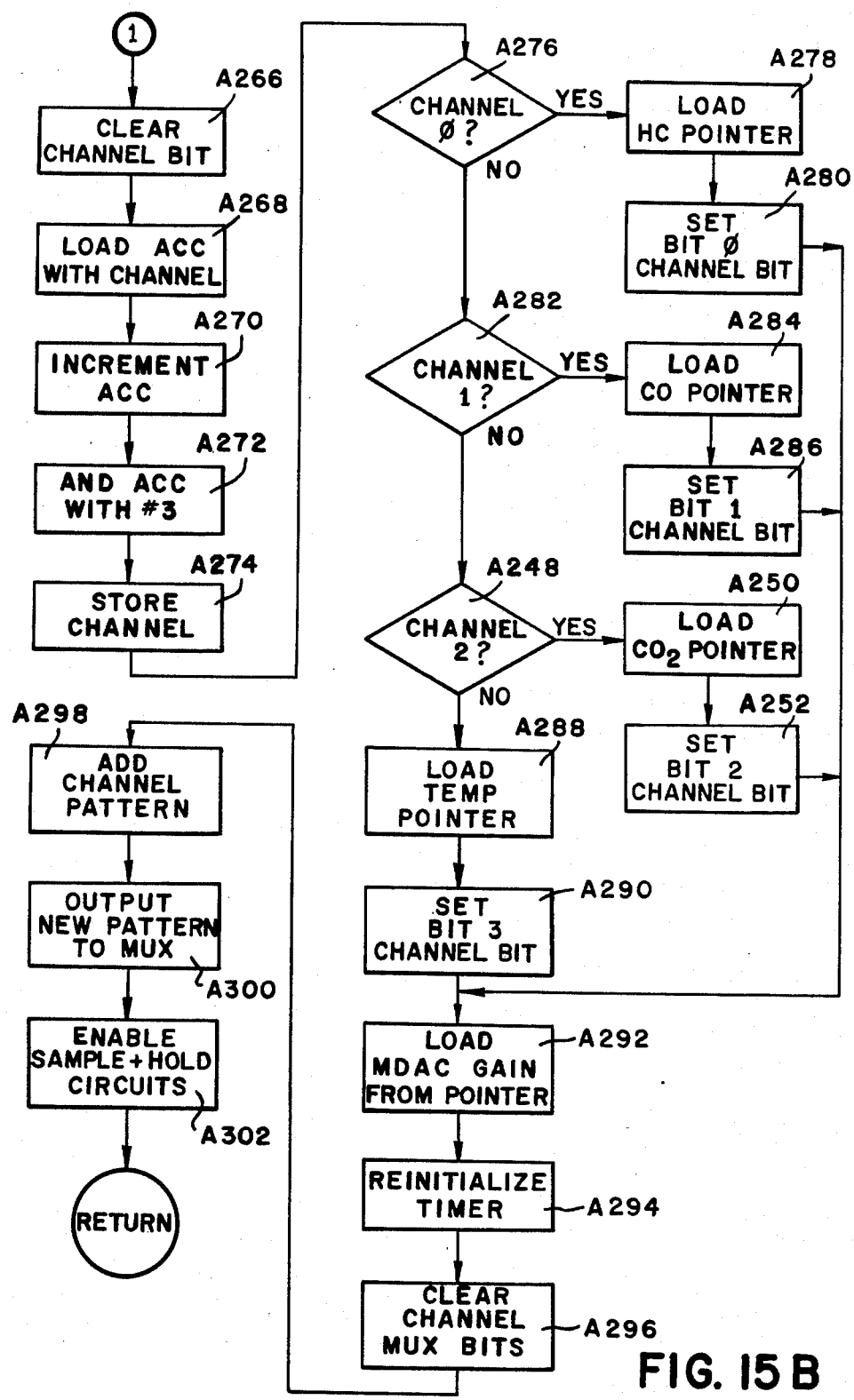

The interrupt routine which is entered once every 10 milliseconds upon the hardware timer interrupt is illustrated in a detailed flow chart in FIGS. 15A and 15B. The first two operations of the interrupt routine are to determine the status of the front panel bit (output of MUX 108), which is read through the multiplexer 108 at pin PA4, and the comparator bit, which is read at pin PA3 of the microprocessor 90. Initially, in block A216 the routine loads the accumulator of the microprocessor 90 with the contents of a location labelled FRONT PANEL storing the status of the front panel bit. Next, the pin PA4 is tested in block A218 to determine its state. If the bit is on, then the channel bit is ORed with the accumulator in block A224. If the bit is off, then the channel bit is complemented in block A220 and ANDed with the accumulator in block A222. These operations update the contents of the location FRONT PANEL to the current state of the signal read from pin PA4. The results from logical operations of block A222 or block A224 are stored in the location labeled FRONT PANEL in block A226. The front panel bit at pin PA4 is, therefore, set in the particular channel location being addressed by the demultiplexer 108 such that the location labelled FRONT PANEL will store the results for all four channels to indicate whether or not the electronic calibration is in operation at $Y_0$, whether the $CO_2$ channel is greater than a predetermined offset at $Y_1$, and whether there is a zero command at $Y_2$, and whether $Y_3$ is high or low. In the embodiment shown in FIG. 4B, $Y_3$ is grounded and should always be low. However, this signal line can be used as a configuration indication or other optional signal as needed.

A similar routine reads the comparator bit at pin PA3 which starts in block A228 by loading the accumulator with the contents of the location labeled COMPARATOR. In block A230 the system reads pin PA3 to determine the state of the comparator 106. If the comparator state pin PA3 is high, then the channel bit is ORed with the accumulator in block A136 and, conversely, if the comparator state is low, the channel bit is complemented and then ANDed with the accumulator in blocks A232 and A234. Thereafter, the results are stored in the location labeled comparator in block A238. These operations update the contents of the location COMPARATOR to the current state of the signal read from pin PA3. For each one of the analyzing channels (0–2) and the temperature channel, this provides an indication once every 10 milliseconds of the status of the comparator 106 for that particular channel. The location COMPARATOR may then be read in the other portions of the program and is used as a RAM image of the comparator output for each of the four channels. The image is updated on every loop through the interrupt routine.

After updating the locations FRONT PANEL and COMPARATOR (images); the system disables the inputs to the sample and hold circuits in block A240. This operation is accomplished by bringing pin PA2 to a high logic level which is inverted in an inverter U7-8,9 and applied to the inhibit input INH of the multiplexer 22. The inhibit signal tristates the output of the multiplexer 22 such that the voltage on the capacitors of the sample and hold circuits are maintained at their last value. This operation is to prepare for changing channels and allows the system to come to a steady state before the input voltages multiplied by the new gain and channel are applied to the sample and hold circuits, thereby reducing any noise or transient signals which may be propagated by the MDAC 21 upon switching.

In the next blocks A242–A264 the timers are updated and the blink timer changed. In block A242 the hardware timer is incremented, while in block A244 the blink timer is incremented. Thereafter, in block A246 the propagation timer is incremented and the blink flag tested in block A254. If the blink flag is not true, then there is no need to determine whether it is appropriate to change the state of the ready line. If the blink flag is true, the blink operation is accomplished by toggling the ready line during times when the blink flag is true at one half second intervals. Therefore, in block A256 the blink timer is compared to a constant (50) to determine if a half second has elapsed. If the time has elapsed, then the program continues to block A260, otherwise it returns to the main path at block A266. If a half second has passed, the blink timer is cleared in block A260 and the ready line tested in block A262. The ready bit is inverted in blocks A258 and A264 by setting the bit if it is cleared, or by clearing the bit if it is set, thus being on for a half second and then being off for a half second. The program then returns to the main path at block A266 to await the passage of another half second.

Next, the program will determine the next channel which should be selected by the multiplexer 22 and the demultiplexers 20, 104, and 108. The channels which are selected by the multiplexers are channels 0–3 corresponding to the HC channel, CO channel, $CO_2$ channel, and temperature channel, respectively. In block A266 the location channel bit is cleared, and in block A268 the accumulator is loaded with the contents of the location channel. The accumulator is then incremented in block A270 to choose the next channel and ANDed with a mask (11) in block A272. The result is stored back into the location channel in block A274. This operation will cause an incrementation of the channel select number from 0-3 and then a repeat of the sequence.

A series of tests are then executed to determine the presently addressed channel and to set up a pointer to the calculated MDAC gain which is to be used for that channel. In block A276 the location channel is tested to determine if it is zero. If the answer is affirmative, then the program branches to block A278 where the index register X is loaded with a pointer directed to the MDAC gain for the HC channel. Next, in block A280 bit 0 of the location channel bit is set. If the contents of the location channel are equal to a one instead of zero, then in block A282 the program continues at block A284 where the index register X is loaded with a pointer indicating the location of the MDAC gain for the CO channel. Thereafter, the location channel bit is modified by setting bit 1 of that word in block A286. However, if the location channel contains a two, then negative branches from blocks A276 and A282 will cause the test in block A248 to be executed. An affirmative channel 2 branch causes the index register X to be loaded with the $CO_2$ pointer in block A250 and bit 2 to be set in the location channel bit in block A252. If the channel location is none of channels 0, 1 and 2, then the channel location must contain an indication of the temperature channel (3) and, therefore, in block A288 the temperature pointer is loaded into the index register X. Next in block A290, bit 3 of the location channel bit is set to indicate that the input to the temperature channel is to be measured during this time interval.

After setting the index pointer and the channel bit depending upon the value of the location channel, the program in block A292 loads the MDAC 21 with the gain from the location determined by the pointer. Thereafter, the timer is reinitialized in block A294. The last part of the interrupt routine includes setting the new multiplexer channel selection on bits PA0, PA1 of the output of the microprocessor 90. In block A296 the multiplexer address bits are first cleared and then the channel pattern from the location channel bit are added to the location storing the multiplexer address bits in block A298. The new pattern is then output to the multiplexers in block A300, and the sample and hold circuits are enabled by bringing pin PA2 of the microprocessor 90 high. The interrupt routine thereafter, reverts to the location from which the routine was called.

While a preferred embodiment of the invention has been illustrated, it will be obvious to those skilled in the art that various modifications and changes may be made thereto without departing from the spirit and scope of the invention. Specifically, the thermistor 118 can be placed on either side of the MDAC 21, as these elements are connected in the same leg of a bridge which to be balanced. Thus, the resistor 122 connected to the output of the multiplexer 22 can be the temperature sensitive element. Also, as stated above, other gases can be analyzed. It is also possible to provide other time delays. For example, 20 minutes between zeroing appears is practical. It is also possible to operate without a host in certain embodiments. In this case the pump and solenoid signal may operate a relay or SCR to actuate drivers for the pump 126 and solenoid 128.

The following appendix is a machine language listing of the system program and subroutines described for FIGS. 8-15.

```
              33 *
              34 *THERMISTOR ARRAYS IN THE ZERO PAGE
              35 *
0080 00       36 LTEMP_TABLE    FCB         00H
0081 00       37                FCB         00H
0082 00       38                FCB         00H
0083 00       39                FCB         00H
0084 00       40                FCB         00H
0085 00       41                FCB         00H
0086 00       42                FCB         00H
0087 00       43                FCB         00H
0088 00       44                FCB         00H
0089 00       45                FCB         00H
008A 00       46                FCB         00H
008B 00       47                FCB         00H
008C 00       48                FCB         00H
008D 00       49                FCB         00H
008E 00       50                FCB         00H
008F 00       51                FCB         00H
0090 00       52 HTEMP_TABLE    FCB         00H
0091 00       53                FCB         00H
0092 00       54                FCB         00H
0093 00       55                FCB         00H
0094 02       56                FCB         02H
0095 06       57                FCB         06H 0096 0A       58                FCB         0AH
0097 0E       59                FCB         0EH
0098 12       60                FCB         12H
0099 16       61                FCB         16H
009A 1A       62                FCB         1AH
009B 1E       63                FCB         1EH
009C 22       64                FCB         22H
009D 26       65                FCB         26H
009E 2A       66                FCB         2AH
009F 2E       67                FCB         2EH
              68 ******************************************************************
              69 *********************BEGIN EXECUTABLE CODE************************
              70 ******************************************************************
00A0 A6 E7    71 INITIALIZE     LDA         #PORTA_DDR_WORD *SPECIFY PORT DATA DIRECTIONS
00A2 B7 04    72                STA         PORTA_DDR
00A4 A6 FF    73                LDA         #PORTB_DDR_WORD
```

```
00A6 B7 05      74        STA     PORTB_DDR
00A8 A6 FF      75        LDA     #PORTC_DDR_WORD
00AA B7 06      76        STA     PORTC_DDR
00AC A6 00      77        LDA     #A_INIT             *INITIAL PORT A PATTERN
00AE B7 00      78        STA     PORTA
00B0 A6 00      79        LDA     #B_INIT             *INITIAL PORT B PATTERN
00B2 B7 01      80        STA     PORTB
00B4 A6 00      81        LDA     #C_INIT             *INITIAL PORT C PATTERN
00B6 B7 02      82        STA     PORTC
00B8 A6 14      83        LDA     #FULL_TIME          *FULL WARMUP TIME
00BA B7 23      84        STA     WARMUP_TIME
                85
00BC AE 27      86        LDX     #HC_POINTER
00BE A6 01      87        LDA     #1
00C0 F7         88        STA     INPUT,X
00C1 A6 00      89        LDA     #0
00C3 E7 02      90        STA     HIBYTE,X
00C5 E7 01      91        STA     LOBYTE,X
00C7 AE 2A      92        LDX     #CO_POINTER
00C9 A6 02      93        LDA     #2
00CB F7         94        STA     INPUT,X
00CC A6 00      95        LDA     #0
00CE E7 02      96        STA     HIBYTE,X
00D0 E7 01      97        STA     LOBYTE,X
00D2 AE 2D      98        LDX     #CO2_POINTER
00D4 A6 04      99        LDA     #4
00D6 F7        100        STA     INPUT,X
00D7 A6 00     101        LDA     #0
00D9 E7 02     102        STA     HIBYTE,X
00DB E7 01     103        STA     LOBYTE,X
00DD AE 30     104        LDX     #TEMP_POINTER
00DF A6 08     105        LDA     #8
00E1 F7        106        STA     INPUT,X
00E2 A6 00     107        LDA     #0
00E4 E7 02     108        STA     HIBYTE,X
00E6 E7 01     109        STA     LOBYTE,X
               110
00E8 4F        111        CLRA                        *ZERO CRITICAL VARIABLES
00E9 B7 13     112        STA     SECONDS
00EB B7 14     113        STA     MINUTES
00ED B7 15     114        STA     TIMER
00EF B7 16     115        STA     BLINK_TIMER
00F1 B7 17     116        STA     PROP_TIMER
00F3 B7 18     117        STA     ZERO_FAIL_FLAG
00F5 B7 19     118        STA     TEMP_FAIL_FLAG
00F7 B7 1A     119        STA     BLINK_FLAG
00F9 B7 1B     120        STA     COMPARATOR
00FB B7 1C     121        STA     FRONT_PANEL
00FD A6 07     122        LDA     #TIMER_CNTRL_WORD  *SET UP TIMER
00FF B7 09     123        STA     TIMER_CNTRL
0101 A6 50     124        LDA     #TEN_MS            *TIMER COUNTS 10 MILLISEC INTERVALS
0103 B7 08     125        STA     TIMER_DATA
0105 9A        126        CLI                        *ENABLE INTERRUPTS
               127 ************************************************************
0106 1D 10     128 WARMUP BCLR    ZERO_REQ_BIT,BYTEA *SET UP FRONT PANEL
0108 1E 10     129        BSET    PUMP_SOL_BIT,BYTEA
010A 1B 10     130        BCLR    READY_BIT,BYTEA
010C 3F 13     131        CLR     SECONDS
010E 3F 14     132        CLR     MINUTES
0110 3F 15     133        CLR     TIMER
0112 CD 05CB   134        JSR     PROP_WAIT
0115 B6 15     135 WM3    LDA     TIMER              *WAIT FOR WARMUP
0117 A1 64     136        CMPA    #ONE_SECOND
0119 25 FA     137        BLO     WM3
011B 3C 13     138        INC     SECONDS
011D 3F 15     139        CLR     TIMER
011F B6 13     140        LDA     SECONDS
0121 A1 3C     141        CMPA    #ONE_MINUTE
0123 25 F0     142        BLO     WM3

012F 3F 13     150 NO_SHORT CLR   SECONDS
0131 3C 14     151        INC     MINUTES
0133 B6 14     152        LDA     MINUTES
0135 B1 23     153        CMPA    WARMUP_TIME
0137 25 DC     154        BLO     WM3
0139 AE 2A     155        LDX     #CO_POINTER        *SAR ON CO CHAN
013B CD 0219   156 WM1    JSR     SAR                *INITIALIZE CO CHAN
013E CD 0495   157        JSR     OFFSET_CO          *OFFSET BY MAX ALLOWABLE DRIFT
0141 E6 01     158        LDA     LOBYTE,X           *SATURATE THE OUTPUT DURING DRIFT WAIT
0143 B7 25     159        STA     SAVE1
0145 E6 02     160        LDA     HIBYTE,X
0147 B7 26     161        STA     SAVE2
0149 6F 01     162        CLR     LOBYTE,X
014B 6F 02     163        CLR     HIBYTE,X
014D 3F 15     164        CLR     TIMER
014F 3F 13     165        CLR     SECONDS
0151 B6 15     166 WM2    LDA     TIMER              *WAIT FOR ONE DRIFT INTERVAL
0153 A1 64     167        CMPA    #ONE_SECOND
```

```
0155 25 FA      168             BLO     WM2
0157 3C 13      169             INC     SECONDS
0159 3F 15      170             CLR     TIMER
015B B6 13      171             LDA     SECONDS
015D A1 3C      172             CMPA    #ONE_MINUTE
015F 25 F0      173             BLO     WM2
0161 3F 13      174             CLR     SECONDS
0163 3C 14      175             INC     MINUTES
0165 B6 14      176             LDA     MINUTES
0167 A1 07      177             CMPA    #DRIFT_TIME
0169 25 E6      178             BLO     WM2
016B B6 25      179             LDA     SAVE1           *RECOVER DAC WORD
016D E7 01      180             STA     LOBYTE,X
016F B6 26      181             LDA     SAVE2
0171 E7 02      182             STA     HIBYTE,X
0173 CD 05CB    183             JSR     PROP_WAIT       *WAIT FOR PROPAGATION DELAY
0176 F6         184             LDA     INPUT,X         *READ CO INPUT
0177 B5 1B      185             BIT     COMPARATOR
0179 26 C0      186             BNE     WM1             *RECYCLE IF TOO MUCH DRIFT
                187     ***********************************************************************
017B 1D 10      188 ZERO        BCLR    ZERO_REQ_BIT,BYTEA *SET UP FRONT PANEL
017D 1E 10      189             BSET    PUMP_SOL_BIT,BYTEA
017F 1B 10      190             BCLR    READY_BIT,BYTEA
0181 AE 2A      191             LDX     #CO_POINTER
0183 CD 0219    192             JSR     SAR
0186 AE 2D      193             LDX     #CO2_POINTER
0188 CD 0219    194             JSR     SAR
018B AE 27      195             LDX     #HC_POINTER
018D CD 0219    196             JSR     SAR
0190 AE 30      197             LDX     #TEMP_POINTER
0192 CD 039C    198             JSR     SAR_TEMP
0195 B6 18      199             LDA     ZERO_FAIL_FLAG
0197 27 02      200             BEQ     ZERO1
0199 20 04      201             BRA     ZERO_REQUEST    *FAILED, GOTO ZERO REQ
019B 3F 19      202 ZERO1       CLR     TEMP_FAIL_FLAG
019D 20 44      203             BRA     NORMAL          *ZERO OK, RETURN TO NORMAL PROCESSING
                204     ***********************************************************************
019F 1C 10      205 ZERO_REQUEST BSET   ZERO_REQ_BIT,BYTEA *SET UP FRONT PANEL
01A1 1F 10      206             BCLR    PUMP_SOL_BIT,BYTEA
01A3 1A 10      207             BSET    READY_BIT,BYTEA
01A5 A6 FF      208             LDA     #TRUE           *BLINKING READY LIGHT
01A7 B7 1A      209             STA     BLINK_FLAG
01A9 3F 16      210             CLR     BLINK_TIMER
01AB B6 1C      211 ZR1         LDA     FRONT_PANEL     *WAIT FOR ZERO COMMAND
01AD A5 04      212             BIT     #4              *ZERO COMMAND BIT POSITION
01AF 26 FA      213             BNE     ZR1
                214     ***********************************************************************
01B1 1D 10      215 CO2_WAIT    BCLR    ZERO_REQ_BIT,BYTEA *SET UP FRONT PANEL
01B3 1F 10      216             BCLR    PUMP_SOL_BIT,BYTEA
01B5 1A 10      217             BSET    READY_BIT,BYTEA
01B7 A6 FF      218             LDA     #TRUE           *BLINKING READY LIGHT
01B9 B7 1A      219             STA     BLINK_FLAG
01BB 3F 16      220             CLR     BLINK_TIMER
01BD 031C FD    221             BRCLR   CO2_COMP_BIT,FRONT_PANEL,$  *WAIT IF CO2 HIGH
01C0 011C FD    222             BRCLR   CAL_BIT,FRONT_PANEL,$       *WAIT IF CAL ENGAGED
                223     ***********************************************************************
01C3 1D 10      224 PURGE       BCLR    ZERO_REQ_BIT,BYTEA *SET UP FRONT PANEL
01C5 1E 10      225             BSET    PUMP_SOL_BIT,BYTEA
01C7 1B 10      226             BCLR    READY_BIT,BYTEA
01C9 A6 00      227             LDA     #FALSE          *TURN OFF BLINKING LIGHT
01CB B7 1A      228             STA     BLINK_FLAG
01CD 3F 15      229             CLR     TIMER
01CF 3F 13      230             CLR     SECONDS
01D1 B6 15      231 PURGE1      LDA     TIMER
01D3 A1 64      232             CMPA    #ONE_SECOND
01D5 25 FA      233             BLO     PURGE1
01D7 3C 13      234             INC     SECONDS
01D9 3F 15      235             CLR     TIMER
01DB B6 13      236             LDA     SECONDS
01DD A1 0F      237             CMP     #PURGE_TIME
01DF 25 F0      238             BLO     PURGE1
01E1 20 98      239             BRA     ZERO
                240     ***********************************************************************
01E3 1D 10      241 NORMAL      BCLR    ZERO_REQ_BIT,BYTEA *SET UP FRONT PANEL
01E5 1F 10      242             BCLR    PUMP_SOL_BIT,BYTEA
01E7 1A 10      243             BSET    READY_BIT,BYTEA
01E9 3F 15      244             CLR     TIMER           *INITIALIZE TIMERS
01EB 3F 13      245             CLR     SECONDS
01ED 3F 14      246             CLR     MINUTES
01EF B6 15      247 NORM1       LDA     TIMER           *TIME FOR AUTO ZERO?
01F1 A1 64      248             CMPA    #ONE_SECOND
01F3 25 16      249             BLO     NORM2
01F5 3F 15      250             CLR     TIMER
01F7 3C 13      251             INC     SECONDS
01F9 B6 13      252             LDA     SECONDS
01FB A1 3C      253             CMPA    #ONE_MINUTE
01FD 25 0C      254             BLO     NORM2
```

```
01FF 3F 13      255              CLR       SECONDS
0201 3C 14      256              INC       MINUTES
0203 B6 14      257              LDA       MINUTES
0205 A1 0F      258              CMPA      #ZERO_INTERVAL
0207 25 02      259              BLO       NORM2
0209 20 94      260              BRA       ZERO_REQUEST
020B 044C 02    261   NORM2      BRSET     ZERO_COMM_BIT,FRONT_PANEL,NORM3
020E 20 A1      262              BRA       CO2_WAIT
0210 CD 04B8    263   NORM3      JSR       CHECK_TEMP
0213 B6 19      264              LDA       TEMP_FAIL_FLAG
0215 26 88      265              BNE       ZERO_REQUEST
0217 20 D6      266              BRA       NORM1
                267   ************************SUBROUTINES***********************************
0219 3F 18      268   SAR        CLR       ZERO_FAIL_FLAG
021B A6 FF      269              LDA       #0FFH            *DAC WORD TO 0FFFH
021D E7 01      270              STA       LOBYTE,X
021F E7 02      271              STA       HIBYTE,X
0221 CD 05CB    272              JSR       PROP_WAIT        *WAIT FOR PROPAGATION DELAY
0224 F6         273              LDA       INPUT,X
0225 B4 1B      274              AND       COMPARATOR
0227 26 03      275              BNE       SIG_OK
0229 CC 05C0    276              JMP       SYS_FAULT        *IF NOT NEGATIVE, SOMETHING WRONG
022C E6 02      277   SIG_OK     LDA       HIBYTE,X
022E A4 7F      278              AND       #07FH            *TURN OFF MSB
0230 E7 02      279              STA       HIBYTE,X
0232 CD 05CB    280              JSR       PROP_WAIT        *WAIT FOR PROPAGATION DELAY
0235 F6         281              LDA       INPUT,X
0236 B4 1B      282              AND       COMPARATOR
0238 26 06      283              BNE       BIT10
023A E6 02      284              LDA       HIBYTE,X
023C AA 80      285              ORA       #80H             *TURN ON MSB IF POSITIVE.
023E E7 02      286              STA       HIBYTE,X
0240 E6 02      287   BIT10      LDA       HIBYTE,X
0242 A4 BF      288              AND       #0BFH            *TURN OFF BIT 10
0244 E7 02      289              STA       HIBYTE,X
0246 CD 05CB    290              JSR       PROP_WAIT        *WAIT FOR PROPAGATION DELAY
0249 F6         291              LDA       INPUT,X
024A B4 1B      292              AND       COMPARATOR
024C 26 06      293              BNE       BIT9
024E E6 02      294              LDA       HIBYTE,X
0250 AA 40      295              ORA       #40H             *TURN ON BIT IF POSITIVE
0252 E7 02      296              STA       HIBYTE,X
0254 E6 02      297   BIT9       LDA       HIBYTE,X
0256 A4 DF      298              AND       #0DFH            *TURN OFF BIT 9
0258 E7 02      299              STA       HIBYTE,X
025A CD 05CB    300              JSR       PROP_WAIT        *WAIT FOR PROPAGATION DELAY
025D F6         301              LDA       INPUT,X
025E B4 1B      302              AND       COMPARATOR
0260 26 06      303              BNE       BIT8
0262 E6 02      304              LDA       HIBYTE,X
0264 AA 20      305              ORA       #20H             *TURN ON BIT IF POSITIVE
0266 E7 02      306              STA       HIBYTE,X
0268 E6 02      307   BIT8       LDA       HIBYTE,X
026A A4 EF      308              AND       #0EFH            *TURN OFF BIT 8
026C E7 02      309              STA       HIBYTE,X
026E CD 05CB    310              JSR       PROP_WAIT        *WAIT FOR PROPAGATION DELAY
0271 F6         311              LDA       INPUT,X
0272 B4 1B      312              AND       COMPARATOR
0274 26 06      313              BNE       BIT7
0276 E6 02      314              LDA       HIBYTE,X
0278 AA 10      315              ORA       #10H             *TURN ON BIT IF POSITIVE
027A E7 02      316              STA       HIBYTE,X
027C E6 02      317   BIT7       LDA       HIBYTE,X
027E A4 F7      318              AND       #0F7H            *TURN OFF BIT 7
0280 E7 02      319              STA       HIBYTE,X
0282 CD 05CB    320              JSR       PROP_WAIT        *WAIT FOR PROPAGATION DELAY
0285 F6         321              LDA       INPUT,X
0286 B4 1B      322              AND       COMPARATOR
0288 26 06      323              BNE       BIT6
028A E6 02      324              LDA       HIBYTE,X
028C AA 08      325              ORA       #08H             *TURN ON BIT IF POSITIVE
028E E7 02      326              STA       HIBYTE,X
0290 E6 02      327   BIT6       LDA       HIBYTE,X
0292 A4 FB      328              AND       #0FBH            *TURN OFF BIT 6
0294 E7 02      329              STA       HIBYTE,X
0296 CD 05CB    330              JSR       PROP_WAIT        *WAIT FOR PROPAGATION DELAY
0299 F6         331              LDA       INPUT,X
029A B4 1B      332              AND       COMPARATOR
029C 26 06      333              BNE       BIT5
029E E6 02      334              LDA       HIBYTE,X
02A0 AA 04      335              ORA       #04H             *TURN ON BIT IF POSITIVE
02A2 E7 02      336              STA       HIBYTE,X
02A4 E6 02      337   BIT5       LDA       HIBYTE,X
02A6 A4 FD      338              AND       #0FDH            *TURN OFF BIT 5
02A8 E7 02      339              STA       HIBYTE,X
02AA CD 05CB    340              JSR       PROP_WAIT        *WAIT FOR PROPAGATION DELAY
02AD F6         341              LDA       INPUT,X
02AE B4 1B      342              AND       COMPARATOR
```

```
02B0 26 06      343              BNE      BIT4
02B2 E6 02      344              LDA      HIBYTE,X
02B4 AA 02      345              ORA      #02H              *TURN ON BIT IF POSITIVE
02B6 E7 02      346              STA      HIBYTE,X
02B8 E6 02      347  BIT4        LDA      HIBYTE,X
02BA A4 FE      348              AND      #0FEH             *TURN OFF BIT 4
02BC E7 02      349              STA      HIBYTE,X
02BE CD 05CB    350              JSR      PROP_WAIT         *WAIT FOR PROPAGATION DELAY
02C1 F6         351              LDA      INPUT,X
02C2 B4 1B      352              AND      COMPARATOR
02C4 26 06      353              BNE      BIT3
02C6 E6 02      354              LDA      HIBYTE,X
02C8 AA 01      355              ORA      #01H              *TURN ON BIT IF POSITIVE
02CA E7 02      356              STA      HIBYTE,X
02CC E6 01      357  BIT3        LDA      LOBYTE,X
02CE A4 07      358              AND      #007H             *TURN OFF BIT 3
02D0 E7 01      359              STA      LOBYTE,X
02D2 CD 05CB    360              JSR      PROP_WAIT         *WAIT FOR PROPAGATION DELAY
02D5 F6         361              LDA      INPUT,X
02D6 B4 1B      362              AND      COMPARATOR
02D8 26 06      363              BNE      BIT2
02DA E6 01      364              LDA      LOBYTE,X
02DC AA 08      365              ORA      #08H              *TURN ON BIT IF POSITIVE
02DE E7 01      366              STA      LOBYTE,X
02E0 E6 01      367  BIT2        LDA      LOBYTE,X
02E2 A4 0B      368              AND      #00BH             *TURN OFF BIT 2
02E4 E7 01      369              STA      LOBYTE,X
02E6 CD 05CB    370              JSR      PROP_WAIT         *WAIT FOR PROPAGATION DELAY
02E9 F6         371              LDA      INPUT,X
02EA B4 1B      372              AND      COMPARATOR
02EC 26 08      373              BNE      BIT1
02EE E6 01      374              LDA      LOBYTE,X
02F0 E7 01      375              STA      LOBYTE,X
02F2 AA 04      376              ORA      #04H              *TURN ON BIT IF POSITIVE
02F4 E7 01      377              STA      LOBYTE,X
02F6 E6 01      378  BIT1        LDA      LOBYTE,X
02F8 A4 0D      379              AND      #00DH             *TURN OFF BIT 1
02FA E7 01      380              STA      LOBYTE,X
02FC CD 05CB    381              JSR      PROP_WAIT         *WAIT FOR PROPAGATION DELAY
02FF F6         382              LDA      INPUT,X
0300 B4 1B      383              AND      COMPARATOR
0302 26 06      384              BNE      BIT0
0304 E6 01      385              LDA      LOBYTE,X
0306 AA 02      386              ORA      #02H              *TURN ON BIT IF POSITIVE
0308 E7 01      387              STA      LOBYTE,X
030A E6 01      388  BIT0        LDA      LOBYTE,X
030C A4 0E      389              AND      #00EH             *TURN OFF BIT 0
030E E7 01      390              STA      LOBYTE,X
0310 CD 05CB    391              JSR      PROP_WAIT         *WAIT FOR PROPAGATION DELAY
0313 F6         392              LDA      INPUT,X
0314 B4 1B      393              AND      COMPARATOR
0316 26 06      394              BNE      SAR_OUT
0318 E6 01      395              LDA      LOBYTE,X
031A AA 01      396              ORA      #01H              *TURN ON BIT IF POSITIVE
031C E7 01      397              STA      LOBYTE,X
                398  *
                399  *END OF SAR - CHECK ZERO INTEGRITY BY ADDING, SUBTRACTING 1/256 OF DAC WORD
                400  *
031E E6 01      401  SAR_OUT     LDA      LOBYTE,X          *SAVE DAC WORD
0320 B7 25      402              STA      SAVE1
0322 E6 02      403              LDA      HIBYTE,X
0324 B7 26      404              STA      SAVE2
0326 46         405              RORA                       *TAKE UPPER FIVE BITS TO EVALUATE
0327 46         406              RORA                       *ZERO NOISE MARGIN
0328 46         407              RORA
0329 A4 0F      408              AND.     #0FH
032B B7 20      409              STA      L_TEMP
032D E6 02      410              LDA      HIBYTE,X
032F 46         411              RORA
0330 46         412              RORA
0331 46         413              RORA
0332 46         414              RORA
0333 46         415              RORA
0334 46         416              RORA
0335 46         417              RORA
0336 A4 01      418              AND      #1
0338 B7 21      419              STA      H_TEMP
033A B6 20      420  LOOP        LDA      L_TEMP
033C E1 01      421              CMP      LOBYTE,X          *OFFSET GREATER THAN DAC LS NIBBLE?
033E 22 08      422              BHI      SAR1
0340 E6 01      423              LDA      LOBYTE,X
0342 B0 20      424              SUB      L_TEMP            *IF NOT, SUBTRACT OFFSET FROM NIBBLE
0344 E7 01      425              STA      LOBYTE,X
0346 20 0E      426              BRA      SAR2
0348 B6 20      427  SAR1        LDA      L_TEMP            *IF SO, SUBTRACT NIBBLE FROM OFFSET
034A E0 01      428              SUB      LOBYTE,X
034C B7 24      429              STA      SAVE
```

| | | | | | | |
|---|---|---|---|---|---|---|
| 034E 6A 02 | 430 | | DEC | HIBYTE,X | *AND BORROW FROM MS BYTE | |
| 0350 A6 0F | 431 | | LDA | #0FH | | |
| 0352 B0 24 | 432 | | SUB | SAVE | *AND SUBTRACT THE REST | |
| 0354 E7 01 | 433 | | STA | LOBYTE,X | | |
| 0356 E6 02 | 434 | SAR2 | LDA | HIBYTE,X | *HIGH BYTE OFFSET SUBTRACT | |
| 0358 B0 21 | 435 | | SUB | H_TEMP | | |
| 035A E7 02 | 436 | | STA | HIBYTE,X | | |
| 035C CD 05D4 | 437 | | JSR | TPROP_WAIT | *WAIT | |
| 035F F6 | 438 | | LDA | INPUT,X | *CHECK COMPARATOR STATE | |
| 0360 B5 1B | 439 | | BIT | COMPARATOR | | |
| 0362 27 06 | 440 | | BEQ | SAR3 | | |
| 0364 A6 FF | 441 | | LDA | #TRUE | *SET FAIL FLAG IF COMPARATOR LOW | |
| 0366 B7 18 | 442 | | STA | ZERO_FAIL_FLAG | | |
| 0368 20 26 | 443 | | BRA | SAR4 | | |
| 036A B6 25 | 444 | SAR3 | LDA | SAVE1 | *RECOVER DAC WORD FOR NEXT TEST | |
| 036C E7 01 | 445 | | STA | LOBYTE,X | | |
| 036E B6 26 | 446 | | LDA | SAVE2 | | |
| 0370 E7 02 | 447 | | STA | HIBYTE,X | | |
| 0372 B6 20 | 448 | | LDA | L_TEMP | *ADD OFFSET AND CHECK | |
| 0374 EB 01 | 449 | | ADD | LOBYTE,X | | |
| 0376 28 04 | 450 | | BHCC | SAR5 | *CHECK FOR CARRY | |
| 0378 6C 02 | 451 | | INC | HIBYTE,X | *PROPAGATE TO HIGH BYTE | |
| 037A A4 0F | 452 | | AND | #0FH | | |
| 037C E7 01 | 453 | SAR5 | STA | LOBYTE,X | | |
| 037E B6 21 | 454 | | LDA | H_TEMP | | |
| 0380 EB 02 | 455 | | ADD | HIBYTE,X | | |
| 0382 E7 02 | 456 | | STA | HIBYTE,X | | |
| 0384 CD 05D4 | 457 | | JSR | TPROP_WAIT | *WAIT | |
| 0387 F6 | 458 | | LDA | INPUT,X | *CHECK COMPARATOR STATE | |
| 0388 B5 1B | 459 | | BIT | COMPARATOR | | |
| 038A 26 04 | 460 | | BNE | SAR4 | | |
| 038C A6 FF | 461 | | LDA | #TRUE | *SET FAIL FLAG IF COMPARATOR HIGH | |
| 038E B7 18 | 462 | | STA | ZERO_FAIL_FLAG | | |
| 0390 B6 25 | 463 | SAR4 | LDA | SAVE1 | *RECOVER DAC WORD | |
| 0392 E7 01 | 464 | | STA | LOBYTE,X | | |
| 0394 B6 26 | 465 | | LDA | SAVE2 | | |
| 0396 E7 02 | 466 | | STA | HIBYTE,X | | |
| 0398 CD 05D4 | 467 | | JSR | TPROP_WAIT | *WAIT | |
| 039B 81 | 468 | | RTS | | | |
| | 469 | * | | | | |
| | 470 | *SAR FOR TEMP INPUT | | | | |
| | 471 | * | | | | |
| 039C A6 FF | 472 | SAR_TEMP | LDA | #0FFH | *DAC WORD TO 0FFFH | |
| 039E E7 01 | 473 | | STA | LOBYTE,X | | |
| 03A0 E7 02 | 474 | | STA | HIBYTE,X | | |
| 03A2 E6 02 | 475 | | LDA | HIBYTE,X | | |
| 03A4 A4 7F | 476 | | AND | #07FH | *TURN OFF MSB | |
| 03A6 E7 02 | 477 | | STA | HIBYTE,X | | |
| 03A8 CD 05CB | 478 | | JSR | PROP_WAIT | *WAIT FOR PROPAGATION DELAY | |
| 03AB F6 | 479 | | LDA | INPUT,X | | |
| 03AC B4 1B | 480 | | AND | COMPARATOR | | |
| 03AE 27 06 | 481 | | BEQ | TBIT10 | | |
| 03B0 E6 02 | 482 | | LDA | HIBYTE,X | | |
| 03B2 AA 80 | 483 | | ORA | #80H | *TURN ON MSB IF POSITIVE | |
| 03B4 E7 02 | 484 | | STA | HIBYTE,X | | |
| 03B6 E6 02 | 485 | TBIT10 | LDA | HIBYTE,X | | |
| 03B8 A4 BF | 486 | | AND | #0BFH | *TURN OFF BIT 10 | |
| 03BA E7 02 | 487 | | STA | HIBYTE,X | | |
| 03BC CD 05CB | 488 | | JSR | PROP_WAIT | *WAIT FOR PROPAGATION DELAY | |
| 03BF F6 | 489 | | LDA | INPUT,X | | |
| 03C0 B4 1B | 490 | | AND | COMPARATOR | | |
| 03C2 27 06 | 491 | | BEQ | TBIT9 | | |
| 03C4 E6 02 | 492 | | LDA | HIBYTE,X | | |
| 03C6 AA 40 | 493 | | ORA | #40H | *TURN ON BIT IF POSITIVE | |
| 03C8 E7 02 | 494 | | STA | HIBYTE,X | | |
| 03CA E6 02 | 495 | TBIT9 | LDA | HIBYTE,X | | |
| 03CC A4 DF | 496 | | AND | #0DFH | *TURN OFF BIT 9 | |
| 03CE E7 02 | 497 | | STA | HIBYTE,X | | |
| 03D0 CD 05CB | 498 | | JSR | PROP_WAIT | *WAIT FOR PROPAGATION DELAY | |
| 03D3 F6 | 499 | | LDA | INPUT,X | | |
| 03D4 B4 1B | 500 | | AND | COMPARATOR | | |
| 03D6 27 06 | 501 | | BEQ | TBIT8 | | |
| 03D8 E6 02 | 502 | | LDA | HIBYTE,X | | |
| 03DA AA 20 | 503 | | ORA | #20H | *TURN ON BIT IF POSITIVE | |
| 03DC E7 02 | 504 | | STA | HIBYTE,X | | |
| 03DE E6 02 | 505 | TBIT8 | LDA | HIBYTE,X | | |
| 03E0 A4 EF | 506 | | AND | #0EFH | *TURN OFF BIT 8 | |
| 03E2 E7 02 | 507 | | STA | HIBYTE,X | | |
| 03E4 CD 05CB | 508 | | JSR | PROP_WAIT | *WAIT FOR PROPAGATION DELAY | |
| 03E7 F6 | 509 | | LDA | INPUT,X | | |
| 03E8 B4 1B | 510 | | AND | COMPARATOR | | |
| 03EA 27 06 | 511 | | BEQ | TBIT7 | | |
| 03EC E6 02 | 512 | | LDA | HIBYTE,X | | |
| 03EE AA 10 | 513 | | ORA | #10H | *TURN ON BIT IF POSITIVE | |
| 03F0 E7 02 | 514 | | STA | HIBYTE,X | | |
| 03F2 E6 02 | 515 | TBIT7 | LDA | HIBYTE,X | | |
| 03F4 A4 F7 | 516 | | AND | #0F7H | *TURN OFF BIT 7 | |

```
03F6 E7 02      517             STA     HIBYTE,X
03F8 CD 05CB    518             JSR     PROP_WAIT   *WAIT FOR PROPAGATION DELAY
03FB F6         519             LDA     INPUT,X
03FC B4 1B      520             AND     COMPARATOR
03FE 27 06      521             BEQ     TBIT6
0400 E6 02      522             LDA     HIBYTE,X
0402 AA 08      523             ORA     #08H         *TURN ON BIT IF POSITIVE
0404 E7 02      524             STA     HIBYTE,X
0406 E6 02      525 TBIT6       LDA     HIBYTE,X
0408 A4 FB      526             AND     #0FBH        *TURN OFF BIT 6
040A E7 02      527             STA     HIBYTE,X
040C CD 05CB    528             JSR     PROP_WAIT    *WAIT FOR PROPAGATION DELAY
040F F6         529             LDA     INPUT,X
0410 B4 1B      530             AND     COMPARATOR
0412 27 06      531             BEQ     TBIT5
0414 E6 02      532             LDA     HIBYTE,X
0416 AA 04      533             ORA     #04H         *TURN ON BIT IF POSITIVE
0418 E7 02      534             STA     HIBYTE,X
041A E6 02      535 TBIT5       LDA     HIBYTE,X
041C A4 FD      536             AND     #0FDH        *TURN OFF BIT 5
041E E7 02      537             STA     HIBYTE,X
0420 CD 05CB    538             JSR     PROP_WAIT    *WAIT FOR PROPAGATION DELAY
0423 F6         539             LDA     INPUT,X
0424 B4 1B      540             AND     COMPARATOR
0426 27 06      541             BEQ     TBIT4
0428 E6 02      542             LDA     HIBYTE,X
042A AA 02      543             ORA     #02H         *TURN ON BIT IF POSITIVE
042C E7 02      544             STA     HIBYTE,X
042E E6 02      545 TBIT4       LDA     HIBYTE,X
0430 A4 FE      546             AND     #0FEH        *TURN OFF BIT 4
0432 E7 02      547             STA     HIBYTE,X
0434 CD 05CB    548             JSR     PROP_WAIT    *WAIT FOR PROPAGATION DELAY
0437 F6         549             LDA     INPUT,X
0438 B4 1B      550             AND     COMPARATOR
043A 27 06      551             BEQ     TBIT3
043C E6 02      552             LDA     HIBYTE,X
043E AA 01      553             ORA     #01H         *TURN ON BIT IF POSITIVE
0440 E7 02      554             STA     HIBYTE,X
0442 E6 01      555 TBIT3       LDA     LOBYTE,X
0444 A4 07      556             AND     #007H        *TURN OFF BIT 3
0446 E7 01      557             STA     LOBYTE,X
0448 CD 05CB    558             JSR     PROP_WAIT    *WAIT FOR PROPAGATION DELAY
044B F6         559             LDA     INPUT,X
044C B4 1B      560             AND     COMPARATOR
044E 27 06      561             BEQ     TBIT2
0450 E6 01      562             LDA     LOBYTE,X
0452 AA 08      563             ORA     #08H         *TURN ON BIT IF POSITIVE
0454 E7 01      564             STA     LOBYTE,X
0456 E6 01      565 TBIT2       LDA     LOBYTE,X
0458 A4 0B      566             AND     #00BH        *TURN OFF BIT 2
045A E7 01      567             STA     LOBYTE,X
045C CD 05CB    568             JSR     PROP_WAIT    *WAIT FOR PROPAGATION DELAY
045F F6         569             LDA     INPUT,X
0460 B4 1B      570             AND     COMPARATOR
0462 27 08      571             BEQ     TBIT1
0464 E6 01      572             LDA     LOBYTE,X
0466 E7 01      573             STA     LOBYTE,X
0468 AA 04      574             ORA     #04H         *TURN ON BIT IF POSITIVE
046A E7 01      575             STA     LOBYTE,X
046C E6 01      576 TBIT1       .LDA    LOBYTE,X
046E A4 0D      577             AND     #00DH        *TURN OFF BIT 1
0470 E7 01      578             STA     LOBYTE,X
0472 CD 05CB    579             JSR     PROP_WAIT    *WAIT FOR PROPAGATION DELAY
0475 F6         580             LDA     INPUT,X
0476 B4 1B      581             AND     COMPARATOR
0478 27 06      582             BEQ     TBIT0
047A E6 01      583             LDA     LOBYTE,X
047C AA 02      584             ORA     #02H         *TURN ON BIT IF POSITIVE
047E E7 01      585             STA     LOBYTE,X
0480 E6 01      586 TBIT0       LDA     LOBYTE,X
0482 A4 0E      587             AND     #00EH        *TURN OFF BIT 0
0484 E7 01      588             STA     LOBYTE,X
0486 CD 05CB    589             JSR     PROP_WAIT    *WAIT FOR PROPAGATION DELAY
0489 F6         590             LDA     INPUT,X
048A B4 1B      591             AND     COMPARATOR
048C 27 06      592             BEQ     TSAR_OUT
048E E6 01      593             LDA     LOBYTE,X
0490 AA 01      594             ORA     #01H         *TURN ON BIT IF POSITIVE
0492 E7 01      595             STA     LOBYTE,X
0494 81         596 TSAR_OUT    RTS                  *MORE LATER
                597 *
                598 *CO OFFSET FOR DRIFT EVALUATION
                599 *
0495 A6 06      600 OFFSET_CO   LDA     #L_OFFSET
0497 E1 01      601             CMP     LOBYTE,X     *OFFSET GREATER THAN DAC LS NIBBLE?
0499 22 08      602             BHI     OC1
049B E6 01      603             LDA     LOBYTE,X
```

```
049D A0 06      604            SUB       #L_OFFSET       *IF NOT, SUBTRACT OFFSET FROM NIBBLE
049F E7 01      605            STA       LOBYTE,X
04A1 20 0E      606            BRA       OC2
04A3 A6 06      607 OC1        LDA       #L_OFFSET       *IF SO, SUBTRACT NIBBLE FROM OFFSET
04A5 E0 01      608            SUB       LOBYTE,X
04A7 B7 24      609            STA       SAVE
04A9 6A 02      610            DEC       HIBYTE,X        *AND BORROW FROM MS BYTE
04AB A6 0F      611            LDA       #0FH
04AD B0 24      612            SUB       SAVE            *AND SUBTRACT THE REST
04AF E7 01      613            STA       LOBYTE,X
04B1 E6 02      614 OC2        LDA       HIBYTE,X        *HIGH BYTE OFFSET SUBTACT
04B3 A0 00      615            SUB       #H_OFFSET
04B5 E7 02      616            STA       HIBYTE,X
04B7 81         617            RTS
                618 *
                619 *TEMPERATURE READER
                620 *
                621 *FIRST, SUBTRACT TEMP OFFSET AND CONFIRM COMPARATOR HIGH (NEGATIVE FROM XDUCER)
04B8 AE 30      622 CHECK_TEMP LDX       #TEMP_POINTER
04BA E6 01      623            LDA       LOBYTE,X        *SAVE DAC WORD
04BC B7 25      624            STA       SAVE1
04BE E6 02      625            LDA       HIBYTE,X
04C0 B7 26      626            STA       SAVE2
04C2 46         627            RORA                      *UPPER FOUR BITS FOR TABLE INDEX
04C3 46         628            RORA
04C4 46         629            RORA
04C5 46         630            RORA
04C6 A4 0F      631            AND       #0FH
04C8 B7 1F      632            STA       TEMP_OFFSET
04CA BE 1F      633            LDX       TEMP_OFFSET
04CC E6 80      634            LDA       LTEMP_TABLE,X
04CE B7 20      635            STA       L_TEMP
04D0 E6 90      636            LDA       HTEMP_TABLE,X
04D2 B7 21      637            STA       H_TEMP
04D4 B6 20      638            LDA       L_TEMP
04D6 AE 30      639            LDX       #TEMP_POINTER
04D8 E1 01      640            CMP       LOBYTE,X        *OFFSET GREATER THAN DAC LS NIBBLE?
04DA 22 08      641            BHI       CT1
04DC E6 01      642            LDA       LOBYTE,X
04DE B0 20      643            SUB       L_TEMP          *IF NOT, SUBTRACT OFFSET FROM NIBBLE
04E0 E7 01      644            STA       LOBYTE,X
04E2 20 0E      645            BRA       CT2
04E4 B6 20      646 CT1        LDA       L_TEMP          *IF SO, SUBTRACT NIBBLE FROM OFFSET
04E6 E0 01      647            SUB       LOBYTE,X
04E8 B7 24      648            STA       SAVE
04EA 6A 02      649            DEC       HIBYTE,X        *AND BORROW FROM MS BYTE
04EC A6 0F      650            LDA       #0FH
04EE B0 24      651            SUB       SAVE            *AND SUBTRACT THE REST
04F0 E7 01      652            STA       LOBYTE,X
04F2 E6 02      653 CT2        LDA       HIBYTE,X        *HIGH BYTE OFFSET SUBTRACT
04F4 B0 21      654            SUB       H_TEMP
04F6 E7 02      655            STA       HIBYTE,X
04F8 CD 05CB    656            JSR       PROP_WAIT       *WAIT
04FB F6         657            LDA       INPUT,X         *CHECK COMPARATOR STATE
04FC B5 1B      658            BIT       COMPARATOR
04FE 26 06      659            BNE       CT3
0500 A6 FF      660            LDA       #TRUE           *SET FAIL FLAG IF COMPARATOR LOW
0502 B7 19      661            STA       TEMP_FAIL_FLAG
0504 20 28      662            BRA       CT4
0506 B6 25      663 CT3        LDA       SAVE1           *RECOVER DAC WORD FOR NEXT TEST
0508 E7 01      664            STA       LOBYTE,X
050A B6 26      665            LDA       SAVE2
050C E7 02      666            STA       HIBYTE,X
050E B6 20      667            LDA       L_TEMP          *ADD OFFSET AND CHECK
0510 EB 01      668            ADD       LOBYTE,X
0512 28 04      669            BHCC      CT5             *CHECK FOR CARRY
0514 6C 02      670            INC       HIBYTE,X        *PROPAGATE TO HIGH BYTE
0516 A4 0F      671            AND       #0FH
0518 E7 01      672 CT5        STA       LOBYTE,X
051A B6 21      673            LDA       H_TEMP
051C EB 02      674            ADD       HIBYTE,X
051E 25 0E      675            BCS       CT4
0520 E7 02      676            STA       HIBYTE,X
0522 CD 05CB    677            JSR       PROP_WAIT       *WAIT
0525 F6         678            LDA       INPUT,X         *CHECK COMPARATOR STATE
0526 B5 1B      679            BIT       COMPARATOR
0528 27 04      680            BEQ       CT4
052A A6 FF      681            LDA       #TRUE           *SET FAIL FLAG IF COMPARATOR HIGH
052C B7 19      682            STA       TEMP_FAIL_FLAG
052E B6 25      683 CT4        LDA       SAVE1           *RECOVER DAC WORD
0530 E7 01      684            STA       LOBYTE,X
0532 B6 26      685            LDA       SAVE2
0534 E7 02      686            STA       HIBYTE,X
0536 81         687            RTS
    <0537>     688 INTERRUPT   EQU       $
                689 *
                690 *READ FRONT PANEL
```

```
                691 *
0537 B6 1C      692              LDA       FRONT_PANEL        *UPDATE FRONT PANEL IMAGE
0539 0900 06    693              BRCLR     FRONT_PANEL_BIT,PORTA,INT7
053C BA 1E      694              ORA       CHANNEL_BIT        *BIT ON
053E B7 1C      695              STA       FRONT_PANEL        *SAVE
0540 20 07      696              BRA       INT8
0542 B6 1E      697 INT7         LDA       CHANNEL_BIT
0544 43         698              COMA                         *BIT OFF
0545 B4 1C      699              AND       FRONT_PANEL        *SAVE
0547 B7 1C      700              STA       FRONT_PANEL
0549 B6 1B      701 INT8         LDA       COMPARATOR
054B 0700 06    702              BRCLR     INPUT_BIT,PORTA,INT9
054E BA 1E      703              ORA       CHANNEL_BIT
0550 B7 1B      704              STA       COMPARATOR         *SAVE
0552 20 07      705              BRA       INT11
0554 B6 1E      706 INT9         LDA       CHANNEL_BIT
0556 43         707              COMA                         *BIT OFF
0557 B4 1B      708              AND       COMPARATOR
0559 B7 1B      709              STA       COMPARATOR         *SAVE
                710 *
                711 *UPDATE SAMPLE/HOLD
                712 *
055B 15 00      713 INT11        BCLR      ENABLE_BIT,PORTA *DISABLE SAMPLE/HOLD
                714 *
                715 *UPDATE TIMERS
                716 *
055D 3C 15      717              INC       TIMER              *BUMP COUNTER
055F 3C 16      718              INC       BLINK_TIMER        *AND BLINKING LIGHT TIME BASE
0561 3C 17      719              INC       PROP_TIMER         *AND PROPAGATION DELAY TIMER
0563 B6 1A      720              LDA       BLINK_FLAG
0565 27 11      721              BEQ       INT4
0567 B6 16      722              LDA       BLINK_TIMER
0569 A1 32      723              CMPA      #HALF_SECOND       *IF SO, HAS IT BEEN 1/2 SEC?
056B 25 0B      724              BLO       INT4
056D 3F 16      725              CLR       BLINK_TIMER        *THEN CLEAR TIMER
056F 0A10 04    726              BRSET     READY_BIT,BYTEA,INT5 *AND TOGGLE READY LINE
0572 1A 10      727              BSET      READY_BIT,BYTEA
0574 20 02      728              BRA       INT4
0576 1B 10      729 INT5         BCLR      READY_BIT,BYTEA
                730 *
                731 *SET UP FOR NEXT CHANNEL
                732 *
0578 3F 1E      733 INT4         CLR       CHANNEL_BIT
057A B6 1D      734              LDA       CHANNEL            *BUMP CHANNEL
057C 4C         735              INCA
057D A4 03      736              AND       #3                 *0-3 ONLY, FOR CHANNEL
057F B7 1D      737              STA       CHANNEL
0581 26 06      738              BNE       INT1
0583 AE 27      739              LDX       #HC_POINTER        *HC CHANNEL
0585 10 1E      740              BSET      0,CHANNEL_BIT      *BIT POSITION TO BE UPDATED
0587 20 18      741              BRA       PROCESS
0589 A1 01      742 INT1         CMPA      #1
058B 26 06      743              BNE       INT2
058D AE 2A      744              LDX       #CO_POINTER        *CO CHANNEL
058F 12 1E      745              BSET      1,CHANNEL_BIT      *BIT POSITION TO BE UPDATED
0591 20 0E      746              BRA       PROCESS
0593 A1 02      747 INT2         CMPA      #2
0595 26 06      748              BNE       INT3
0597 AE 2D      749              LDX       #CO2_POINTER       *CO2 CHANNEL
0599 14 1E      750              BSET      2,CHANNEL_BIT      *BIT POSITION TO BE UPDATED
059B 20 04      751              BRA       PROCESS
059D AE 30      752 INT3         LDX       #TEMP_POINTER      *IF GOT THIS FAR, MUST BE TEMP
059F 16 1E      753              BSET      3,CHANNEL_BIT      *BIT POSITION TO BE UPDATED
05A1 E6 01      754 PROCESS      LDA       LOBYTE,X           *WORD TO DAC
05A3 B7 02      755              STA       PORTC
05A5 E6 02      756              LDA       HIBYTE,X
05A7 B7 01      757              STA       PORTB
                758
                759 *
                760 *REINITIALIZE TIMER, REENGAGE SAMPLE/HOLD
                761 *
05A9 A6 50      762 INT10        LDA       #TEN_MS
05AB B7 08      763              STA       TIMER_DATA
05AD 1F 09      764              BCLR      7,TIMER_CNTRL      *CLEAR INTERRUPT REQUEST
05AF 1D 09      765              BCLR      6,TIMER_CNTRL      *CLEAR INTERRUPT MASK
05B1 B6 10      766              LDA       BYTEA              *UPDATE MUX PATTERN, FRONT PANEL
05B3 A4 FC      767              AND       #11111100B         *CLEAR CHANNEL BITS
05B5 BB 1D      768              ADD       CHANNEL
05B7 A8 03      769              EOR       #00000011B         *NEGATIVE SELECT LOGIC
05B9 B7 10      770              STA       BYTEA              *SAVE PATTERN
05BB B7 00      771              STA       PORTA              *OUTPUT PATTERN
05BD 14 00      772              BSET      ENABLE_BIT,PORTA   *ENABLE SAMPLE/HOLD
05BF 80         773              RTI
                774 *
05C0 3F 00      775 SYS_FAULT    CLR       PORTA              *ALL LIGHTS OFF
05C2 3F 10      776              CLR       BYTEA
05C4 A6 00      777              LDA       #FALSE
```

```
05C6 B7 1A      778             STA     BLINK_FLAG
05C8 9B         779             SEI
05C9 20 F5      780             BRA     SYS_FAULT       *DIE
                781 *
05CB 3F 17      782 PROP_WAIT   CLR     PROP_TIMER      *PROPAGATION DELAY TIMER
05CD B6 17      783 PW1         LDA     PROP_TIMER
05CF A1 0A      784             CMP     #PROP_TIME
05D1 25 FA      785             BLO     PW1
05D3 81         786             RTS
05D4 3F 17      787 TPROP_WAIT  CLR     PROP_TIMER      *PROPAGATION DELAY TIMER
05D6 B6 17      788 PW2         LDA     PROP_TIMER
05D8 A1 64      789             CMP     #TPROP_TIME
05DA 25 FA      790             BLO     PW2
05DC 81         791             RTS
```

Errors= 0

```
DRIFT_TIME      EQU     7                       *IN MIN, FOR CO WARMUP
PURGE_TIME      EQU     15                      *IN SEC
PROP_TIME       EQU     10                      *# OF INTERRUPTS TO WAIT FOR PROPAGATION DELAY
TPROP_TIME      EQU     100                     *LONG WAIT
ZERO_INTERVAL   EQU     15                      *IN MINUTES, TIME BETWEEN AUTO ZEROES
L_OFFSET        EQU     06H                     *LOWER NIBBLE OF CO OFFSET WORD
H_OFFSET        EQU     00H                     *UPPER BYTE OF CO OFFSET WORD
*
*DATA STRUCTURE TEMPLATE
*
INPUT           EQU     0                       *INPUT FROM COMPARATOR
LOBYTE          EQU     INPUT+1                 *DAC WORD LOW BYTE
HIBYTE          EQU     LOBYTE+1                *DAC WORD HIGH BYTE
STRUCT_BYTES    EQU     HIBYTE+1                *# OF BYTE IN STRUCTURES
*
************************RAM EQUATES************************************
*
                ORG     RAM
BYTEA           RMB     1                       *PORT A PATTERN
BYTEB           RMB     1                       *PORT B PATTERN
BYTEC           RMB     1                       *PORT C PATTERN
SECONDS         RMB     1                       *ELAPSED SECONDS
MINUTES         RMB     1                       *ELAPSED MINUTES
TIMER           RMB     1                       *FOREGROUND TIMER VARIABLE
BLINK_TIMER     RMB     1                       *FOREGROUND BLINK TIMER VARIABLE
PROP_TIMER      RMB     1                       *TIMER FOR PROPAGATION DELAY
ZERO_FAIL_FLAG  RMB     1                       *TRUE IF ZERO FAIL
TEMP_FAIL_FLAG  RMB     1                       *TRUE IF TOO MUCH TEMPERATURE DRIFT
BLINK_FLAG      RMB     1                       *TRUE IF BLINKING READY LIGHT
COMPARATOR      RMB     1                       *IMAGE FOR COMPARATOR MUX
FRONT_PANEL     RMB     1                       *IMAGE FOR FRONT PANEL MUX
CHANNEL         RMB     1                       *CHANNEL #
CHANNEL_BIT     RMB     1                       *CORRESPONDING BIT POSITION
TEMP_OFFSET     RMB     1                       *INDEX FOR THEMISTOR TABLES
L_TEMP          RMB     1                       *LOWER NIBBLE RESULT OF TEMP TABLE LOOKUP
H_TEMP          RMB     1                       *UPPER BYTE RESULT OF TEMP TABLE LOOKUP
ZERO_OFFSET     RMB     1                       *ADDED AND SUBTRACTED FROM DAC WORD FOR ZERO CHECK
WARMUP_TIME     RMB     1                       *LOADED WITH SHORT OR NORMAL, DEPENDING ON SWITCH
SAVE            RMB     1                       *WAYWARD BYTES
SAVE1           RMB     1
SAVE2           RMB     1
HC_POINTER      RMB     STRUCT_BYTES            *DATA STRUCTURES
CO_POINTER      RMB     STRUCT_BYTES
CO2_POINTER     RMB     STRUCT_BYTES
TEMP_POINTER    RMB     STRUCT_BYTES

**************************HARDWARE EQUATES**************************
*
PORTA           EQU     0
PORTB           EQU     1
PORTC           EQU     2
PORTD           EQU     3
PORTA_DDR       EQU     4
PORTB_DDR       EQU     5
PORTC_DDR       EQU     6
PORTD_DDR       EQU     7
TIMER_DATA      EQU     8
TIMER_CNTRL     EQU     9
MISCELLANEOUS   EQU     10
PROGRAM_CNTRL   EQU     11

IF      P3=TRUE                 *FOR P3, 28 PIN EPROM VERSION
MOR             EQU     784H                    *MASK OPTION REGISTER
TIMER_INT       EQU     7F8H                    *TIMER INTERRUPT VECTOR
EXT_INT         EQU     7FAH                    *EXTERNAL INTERRUPT VECTOR
SW_INT          EQU     7FCH                    *SOFTWARE INTERRUPT VECTOR
RESET           EQU     7FEH                    *RESET VECTOR

ELSE                            *FOR EPROM U3,U5,R3,R5 VERSIONS (40 PINS)
MOR             EQU     0F38H                   *MASK OPTION REGISTER
```

```
TIMER_INT       EQU     OFF8H           *TIMER INTERRUPT VECTOR
EXT_INT         EQU     OFFAH           *EXTERNAL INTERRUPT VECTOR
SW_INT          EQU     OFFCH           *SOFTWARE INTERRUPT VECTOR
RESET           EQU     OFFEH           *RESET VECTOR
                ENDIF

RAM             EQU     10H             *BEGINNING OF RAM AREA
ROM             EQU     80H             *BEGINNING OF ROM AREA
*
*********************MACRO EQUATES********************************************
*
PORTA_DDR_WORD  EQU     11100111B       *DATA DIRECTION REG PATTERNS
PORTB_DDR_WORD  EQU     0FFH
PORTC_DDR_WORD  EQU     0FFH
A_INIT          EQU     0
B_INIT          EQU     0
C_INIT          EQU     0
TIMER_WORD      EQU     0               *INITIAL TIMER VALUE
TIMER_CNTRL_WORD EQU    00000111B       *CLEAR INT REQUEST,MASK/INTERNAL CLOCK/DIVIDE BY 128 PRESCALE
PUMP_SOL_BIT    EQU     7               *PUMP/SOLENOID CONTROL BIT # (OUTPUT)
ZERO_REQ_BIT    EQU     6               *ZERO REQUEST LINE (OUTPUT)
READY_BIT       EQU     5               *READY LINE (OUTPUT)
******************************************************************************
*CAL_BIT,CO2_COMP_BIT,ZERO_COMM_BIT ARE READ THROUGH FRONT_PANEL BIT          *
*                                                                             *
FRONT_PANEL_BIT EQU     4               *INPUTS FOR: ZERO COMMAND, HIGH CO2, CAL COMMAND *
CAL_BIT         EQU     0               *CAL COMMAND BIT (INPUT)             *
CO2_COMP_BIT    EQU     1               *CO2 COMPARATOR BIT (INPUT)          *
ZERO_COMM_BIT   EQU     2               *ZERO COMMAND BIT (INPUT)            *
WARMUP_BYPASS   EQU     3               *HIGH WILL BYPASS WARMUP             *
******************************************************************************
INPUT_BIT       EQU     3               *BENCH COMPARATOR INPUT
ENABLE_BIT      EQU     2               *S/H MUX ENABLE BIT (OUTPUT)
TEN_MS          EQU     80              * X128 MICROSECS = 10.24 MS
MOR_WORD        EQU     0               *PATTERN FOR MASK OPTION REG
HALF_SECOND     EQU     50              *# OF 10 MS TO MAKE 1/2 SECOND
ONE_SECOND      EQU     100             *# OF 10 MS TO MAKE 1 SECOND
ONE_MINUTE      EQU     60              *# OF SECS/MIN
FULL_TIME       EQU     20              *FULL WARMUP TIME, IN MINUTES
BYPASS_TIME     EQU     5               *ABBREVIATED WARMUP, IF SWITCH ENGAGED
```

What is claimed is:

1. Automatic zeroing apparatus for zeroing an infrared gas analyzer automatically upon the occurrence of preselected conditions to indicate zero in the absence of absorption of infrared radiation by a gas mixture being analyzed, the gas analyzer having a sample cell for containing a gas mixture to be analyzed, source means for directing infrared radiation through the sample cell over a range of wavelengths, direction means responsive to infrared radiation at at least one respective preselected wavelength to produce at least one repective detection signal systematically related to the infrared radiation at the respective preselected wavelength passing through the sample cell from the source means which respective wavelength corresponds to the absorption wavelength characteristic of a respective predetermined gas, and signal processing means responsive to said at least one direction signal for indicating the relative concentration of the respective predetermined gas in the mixture being analyzed, said signal processing means including reference means for producing a reference signal, and output means responsive to said at least one detection signal and said reference signal for outputting an output signal systematically related to the difference between said at least one detection signal and said reference signal, said automatic zeroing apparatus comprising:

means for filling the sample cell with gas substantially nonabsorbent of infrared radiation at the respective characteristic wavelength, comparator means responsive to said output signal for producing an error signal when said output signal differs from zero, and gain control means responsive to said error signal for automatically controlling the signal level of said at least one detection signal to reduce said output signal substantially to zero with said substantially nonabsorbent gas filling the sample cell.

2. Automatic zeroing apparatus for zeroing an infrared gas analyzer automatically upon the occurrence of preselected conditions to indicate zero in the absence of absorption of infrared radiation by a gas mixture being analyzed, the gas analyzer having a sample cell for containing a gas mixture to be analyzed, source means for directing infrared radiation through the sample cell over a range of wavelengths, detection means responsive to infrared radiation at at least one respective preselected wavelength to produce at least one respective detection signal systematically related to the infrared radiation at the respective preselected wavelength passing through the sample cell from the source means which respective wavelength corresponds to the absorption wavelength characteristic of a respective predetermined gas, and signal processing means responsive to said at least one detection signal for indicating the relative concentration of the respective predetermined gas in the mixture being analyzed, said signal processing means including reference means for producing a reference signal, and output means responsive to said at least one detection signal and said reference signal for outputting an output signal systematically related to the difference between said at least one detection signal and said reference signal, said automatic zeroing apparatus comprising:

means for filling the sample cell with gas substantially nonabsorbent of infrared radiation at the respective characteristic wavelength;

comparator means responsive to said output signal for producing an error signal when said output signal differs from zero; and gain control means responsive to said error signal for automatically controlling the signal level of said at least one detection signal to reduce said output signal substantially to zero with said substantially nonabsorbent gas filling the sample cell, said gain control means having a zero mode in which the analyzer is zeroed and a normal mode in which analysis is made and comprising mode control means for placing said gain control means in said zero mode, means for operating said mode control means periodically to place said gain control means in said zero mode periodically, means associated with said zero mode for operating said means for filling to fill said sample cell with said substantially nonabsorbent gas, means in said zero mode responsive to said error signal for adjusting the signal level of said detection signal by a factor to balance said reference signal to reduce said output signal substantially to zero, means for storing a representation of said factor, and means in the normal mode for adjusting the signal level by said factor according to said representation stored from the last preceding zero mode, such that after the zero mode said analyzer remains calibrated in the normal mode in the presence of an absorbing gas being analyzed.

3. Automatic zeroing apparatus according to claim 2 further including means responsive to said output signal for generating a high concentration signal when said output signal exceeds a predetermined limit, and means responsive to said high concentration signal for inhibiting said mode control means from entering said zero mode while the concentration of the respective gas is greater than that corresponding to said predetermined limit.

4. Automatic zeroing apparatus according to claim 3 including electronic calibration means for adding a calibration offset signal to said reference signal during calibration, and means responsive to operation of said electronic calibration means for inhibiting the operation of said mode control means from entering said zero mode during electronic calibration.

5. Automatic zeroing apparatus according to claim 3 wherein said respective gas is carbon dioxide.

6. Automatic zeroing apparatus according to claim 2 further including means under the control of an operator for generating a zero command signal, said mode control means being responsive to said zero command signal to place said gain control means in said zero mode.

7. Automatic zeroing apparatus according to claim 2 wherein said gain control means includes a warm-up mode entered upon start-up of the apparatus and further including means in association with said warm-up mode for operating said means for filling to fill said sample cell with said substantially nonabsorbent gas, means in said warm-up mode responsive to said error signal for periodically adjusting the signal level of said detection signal to drive said output signal substantially to zero, and means responsive to successive adjustments of said signal level for operating said mode control means to place said gain control means in said zero mode when successive adjustments are within a predetermined difference.

8. Automatic zeroing apparatus according to claim 7 wherein said predetermined gas is carbon monoxide.

9. Automatic zeroing apparatus according to claim 2 including electronic calibration means for adding a calibration offset signal to said reference signal during calibration, and means responsive to operation of said electronic calibration means for inhibiting the operation of said mode control means from entering said zero mode during electronic calibration.

10. Automatic zeroing apparatus according to claim 2 further including temperature indicating means responsive to temperature for producing a current temperature signal indicative of ambient temperature, means for storing said temperature signal produced during a zero mode, means responsive to said stored temperature signal for providing first and second temperature offset signals corresponding to the offset of temperature above and below the ambient temperature corresponding to said stored signal by at least one predetermined temperature difference, means operative in the normal mode for comparing said stored temperature offset signal with the current temperature signal to produce a temperature drift signal when said current temperature signal differs from said stored temperature signal stored during the last zero mode by more than said first and second temperature offset signals, and means responsive to said temperature drift signal for operating said mode control means to place said gain control means in said zero mode.

11. Automatic zeroing apparatus according to claim 10 further including means responsive to said output signal for generating a high concentration signal when said output signal exceeds a predetermined limit, and means responsive to said high concentration signal for inhibiting said mode conrol means from entering said zero mode while the concentration of the respective gas is greater than that corresponding to said predetermined limit.

12. Automatic zeroing apparatus according to claim 11 including electronic calibration means for adding a calibration offset signal to said reference signal during calibration, and means responsive to operation of said electronic calibration means for inhibiting the operation of said mode control means from entering said zero mode during electronic calibration.

13. Automatic zeroing apparatus according to claim 11 wherein said respective gas is carbon dioxide.

14. Automatic zeroing apparatus according to claim 10 further including means under the control of an operator for generating a zero command signal, said mode control means being responsive to said zero command signal to place said gain control means in said zero mode.

15. Automatic zeroing apparatus according to claim 10 wherein said gain control means includes a warm-up mode entered upon start-up of the apparatus and further including means in association with said warm-up mode for operating said means for filling to fill said sample cell with said substantially nonabsorbent gas, means in said warm-up mode responsive to said error signal for periodically adjusting the signal level of said detection signal to drive said output signal substantially to zero, and means responsive to successive adjustments of said signal level for operating said mode control means to place said gain control means in said zero mode when successive adjustments are within a predetermined difference.

16. Automatic zeroing apparatus according to claim 15 wherein said predetermined gas is carbon monoxide.

17. Automatic zeroing apparatus according to claim 10 including electronic calibration means for adding a calibration offset signal to said reference signal during calibration, and means responsive to operation of said electronic calibration means for inhibiting the operation of said mode control means from entering said zero mode during electronic calibration.

18. Automatic zeroing apparatus according to any one of claims 2 to 17 wherein there is a plurality of predetermined gases, and said means for adjusting signal level includes means for independently adjusting the signal level in respect to each of said plurality of gases by a respective said factor.

19. Automatic zeroing apparatus according to claim 18 wherein said means for adjusting said signal level comprises a multiplying digital to analog converter for adjusting each said signal level by said respective said factor.

20. Automatic zeroing apparatus according to claim 19 wherein said gain control means includes a digital processor for determining said factors for said multiplying digital to analog converter and for storing said representations of said factors upon completion of zeroing.

21. Automatic zeroing apparatus according to any one of claims 2 to 17 wherein said means for adjusting said signal level comprises a multiplying digital to analog converter for adjusting said signal level by said factor.

22. Automatic zeroing apparatus according to claim 21 wherein said gain control means includes a digital processor for determining said factor for said multiplying digital to analog converter and for storing said representation of said factor upon completion of zeroing.

* * * * *